US008865398B2

(12) United States Patent
Rodgers et al.

(10) Patent No.: US 8,865,398 B2
(45) Date of Patent: Oct. 21, 2014

(54) COMBINATION HEPATITIS C VIRUS ANTIGEN AND ANTIBODY DETECTION METHOD

(75) Inventors: Brian C. Rodgers, Bromley (GB); Graham J. Burch, South Darenth (GB)

(73) Assignee: Abbott Laboratories, Abbott Park, IL (US)

( * ) Notice: Subject to any disclaimer, the term of this patent is extended or adjusted under 35 U.S.C. 154(b) by 223 days.

(21) Appl. No.: 11/846,052

(22) Filed: Aug. 28, 2007

(65) Prior Publication Data

US 2008/0113339 A1   May 15, 2008

Related U.S. Application Data

(60) Provisional application No. 60/841,800, filed on Sep. 1, 2006.

(51) Int. Cl.
| | |
|---|---|
| G01N 33/569 | (2006.01) |
| G01N 33/576 | (2006.01) |
| A61K 39/29 | (2006.01) |
| C07K 16/08 | (2006.01) |
| C07K 16/10 | (2006.01) |

(52) U.S. Cl.
CPC .......... *G01N 33/5767* (2013.01); *C07K 16/109* (2013.01); *G01N 33/56966* (2013.01)
USPC ................ 435/5; 436/536; 530/350; 435/7.1; 435/7.2; 435/70.21

(58) Field of Classification Search
CPC ............... C07K 14/005; C07K 16/109; G01N 33/5767; G01N 2469/20; G01N 2333/186; G01N 33/54306; G01N 2469/10
See application file for complete search history.

(56) References Cited

U.S. PATENT DOCUMENTS

| | | | |
|---|---|---|---|
| 5,910,404 A | 6/1999 | Deleys et al. | |
| 5,981,286 A | 11/1999 | Herrmann et al. | |
| 6,007,982 A | 12/1999 | Deleys et al. | |
| 6,165,730 A | 12/2000 | De Leys | |
| 6,183,949 B1 | 2/2001 | Seidel et al. | |
| 6,235,284 B1 | 5/2001 | Dalbon et al. | |
| 6,379,886 B1 * | 4/2002 | Takahama et al. | 435/5 |
| 6,576,417 B2 | 6/2003 | Deleys et al. | |
| 6,592,871 B1 | 7/2003 | Seidel et al. | |
| 6,596,476 B1 | 7/2003 | Lesniewski et al. | |
| 6,613,530 B1 | 9/2003 | Wienhues et al. | |
| 6,623,921 B2 * | 9/2003 | Aoyagi et al. | 435/5 |
| 6,649,735 B1 | 11/2003 | De Leys | |
| 6,667,387 B1 | 12/2003 | De Leys | |
| 6,709,828 B1 | 3/2004 | De Leys | |
| 6,727,092 B2 | 4/2004 | Shah et al. | |
| 6,780,967 B1 | 8/2004 | Seidel et al. | |
| 6,824,981 B2 * | 11/2004 | Chait et al. | 435/6 |
| 6,855,809 B2 | 2/2005 | Shah et al. | |
| 2003/0108563 A1 | 6/2003 | Bahl | |
| 2003/0152965 A1 | 8/2003 | Bahl | |
| 2004/0072267 A1 | 4/2004 | Rieunier et al. | |
| 2005/0084902 A1 * | 4/2005 | Nokihara et al. | 435/7.1 |

FOREIGN PATENT DOCUMENTS

| | | | | |
|---|---|---|---|---|
| DE | 1083428 | * | 11/2001 | ........... G01N 33/578 |
| EP | 1 083 428 A2 | * | 3/2001 | |
| FR | WO 00/31130 | * | 6/2000 | ............. C07K 14/18 |
| WO | 03/002749 | | 1/2003 | |
| WO | WO03/002749 | | 1/2003 | |
| WO | WO03/095968 | | 11/2003 | |
| WO | 2006/053439 | | 5/2006 | |

OTHER PUBLICATIONS

Siemoneit et al., "Isotype-specific immune response to a single hepatitis C virus core epitope defined by a human monoclonal antibody: diagnostic value and correlation to PCR," Annals of hematology, vol. 69 No. 3, pp. 129-133 (Sep. 1994).*
Jolivet-Reynaud et al. "HCV core immunodominant region analysis using mouse monoclonal antibodies and human sera: characterization of major epitopes useful for antigen detection," Journal of Medical virology, col. 56 No. 4, pp. 300-309 (Dec. 1998).*
Menez et al., "Crystal Structure of a Hydrophobic Immunodominant Antigenic Site on Hepatitis C Virus Core Protein Complexed to Monoclonal Antibody 19D9D6 ," Journal of Immunology, vol. 170 No. 4, pp. 1917-1924 (Feb. 2003).*
Ferroni et al., "Identification of four epitopes in hepatitis C virus core protein," Jorunal of Clinical Microbiology, vol. 31 No. 6, pp. 1586-1591 (Jun. 1993).*
Ahmed et al., "Murine humoral immune response against recombinant structural proteins of hepatitis C virus distinct from those of patients," Microbiology and immunology, vol. 40 No. 2, pp. 169-176 (1996).*
Sato et al., "A sensitive serodiagnosis of hepatitis C virus (HCV) infection with two non-fused peptides: comparison of antibody responses detected with a newly developed assay and a commercial second-generation test," Microbiology and immunology, vol. 37 No. 4, pp. 295-304 (1993).*
Ou-Yang et al. Characterization of monoclonal antibodies against hepatitis C virus nonstructural protein 3: Different antigenic determinants from human B cells. Journal of Medical Virology. vol. 57, Issue 4, pp. 345-350, Apr. 1999.*
Abbott Murex, HCV Ag/Ab Combination, Ref 4J24-03, 4J24-04E D014J24GB (Mar. 2006).

(Continued)

*Primary Examiner* — Michelle S Horning
(74) *Attorney, Agent, or Firm* — Irene M. Reininger

(57) ABSTRACT

An in vitro method that allows detection of hepatitis C by detecting hepatitis C virus (HCV) core protein and antibodies to HCV core protein (anti-core antibodies) in a single assay is provided. Cross-reactivity is eliminated in the method preferably by utilizing short peptides, each of which has an amino acid sequence that corresponds to an immunodominant region of the native core protein but which does not wholly encompass the epitope bound by the antibodies utilized in the method. The method can be used to detect the presence of HCV in a subject, and/or to determine the suitability of donor blood or blood products for transfusion purposes. Also provided are diagnostic kits for carrying out the method and a process for selecting suitable capture peptides and monoclonal antibodies for use in the combination method.

11 Claims, 6 Drawing Sheets

(56) References Cited

OTHER PUBLICATIONS

Allen, et al, Poster, "An HCV Antigen/Antibody Combination Assay Closes the Window of Infection vs Antibody only Assays", Presented in Hong Kong, China (Feb. 2004).

Ansaldi, et al., "Combination hepatitis C virus antigen and antibody immunoassay as a new tool for early diagnosis of infection", Journal of Viral Hepatitis,13, 5-10 (2006).

Bergendahl et al, "On column Tris(2-carboxyethyl)phospine reduction and IC5-maleimide labeling during purification of a RpoC fragment on a nickel-nitrilotriacetic acid column.", Analytical Biochemistry,307, 368-374, (2002).

Bukh, et al., Genetic Heterogeneity of Hepatitis C Virus: Quasispecies and Genotypes, Seminars in Liver Disease, 15(1), 41-63 (1995).

Burch, et al, Poster, "Comparative study of the new Murex microplate HCV Ag/Ab combination assy with antibody only and a competitor's Ag/Ab combination assay", Presented at ISBT, Cape Town ; South Africa (Sep. 2006).

Burns et al, "Selective reduction of disulphides by Tris(2-carboxyethyl)phosphine", J Org Chem.,56, 2648-2650 (1991).

Couroucé, et al., "Efficacy of HCV core antigen detection during the preseroconversion period", Transfusion, 40, 1198-1202 (2000).

Getz, et al., "A Comparison between the Sulfhydryl Reductants Tris(2-carboxyethyl)phosphine and Dithiothreitol for Use in Protein Biochemistry", Analytical Biochemistry, 273, 73-80 (1999).

Hermanson, Bioconjugate Techniques, Academic Press, 83-85 (1996).

Hopf, et al., "Long-term follow-up of posttransfusion and sporadic chronic hepatitis non-A, non-B and frequency of circulating antibodies to hepatitis C virus (HCV)" Journal of Hepatology, 10, 69-76 (1990).

Jové, et al, "Post-transfusional vs. sporadic non-A, non-B chronic hepatitis. A clinico-pathological and evolutive study", Liver, 8, 42-47 (1988).

Lambert, et al, Poster, "Performance features of the new Bio-Rad HCV antigen and antibody assay: monolisa HCV Ag-Ab ultra", IBST Conference in Edinburgh, Scottland (Jul. 2004).

Laperche, et al., "Simultaneous Detection of Hepatitis C Virus (HCV) Core Antigen and Anit-HCV Antibodies Improves the Early Detection of HCV infection", Journal of Clinical Microbiology, 43(8), 3877-3883 (2005).

Laperche, et al., Transfusion, Is an assay for simultaneous detection of hepatitis C virus core antigen and acntibody a valuable alternative to nucleic acid testing?, 45, 1965-1972 (2005).

Miller, et al., "Hepatitis C virus shares amino acid sequence similarity with pestiviruses and flaviviruses as well as members of two plant virus supergroups", PNAS USA,87, 2057-2061 (1990).

Shafer, et al., "Reaction of Tris(2-carboxyethyl)phosphine (TCEP) with Maleimide and α-Haloacyl Groupa: Anomalous Elution of TCEP by Gel Filtration", Analytical Biochemistry 282, 161-164 (2000).

Stuyver, et al, "Classification of hepatitis C viruses based on phylogenetic analysis of the envelope 1 and nonstructural 5B regions and identification of five additional subtypes", Proc. Natl. Acad. Sci. USA,, 91, 10134-10138 (1994).

Weiner, et al., "Variable and Hypervariable Domains Are Found in the Regions of HCV Corresponding to the Flavivirus Envelope and NS1 Proteins and the Pestivirus Envelope Glycoproteins", Virology, 180, 842-848 (1991).

"HCV quasispecies evolution: association with progression to end-stage liver disease in hemophiliacs infected with HCV or HCV/HIV" Qin, H., et al. (Blood) Jan. 15, 2005, vol. 105, No. 2, pp. 533-541 XP-002464016.

PCT International Search Report (PCT/US2007/077065) Mailed Apr. 21, 2008.

* cited by examiner

MSTNPKPQRK TKRNTNRRPQ DVKFPGGGQI VGGVYLLPRR GPRLGVRATR
KTSERSQPRG RRQPIPKARR PEGRTWAPGY PWPLYGNEGC GWAGWLLSPR
GSRPSWGPTD PRRRSRNLGK VIDTTCGFAD LMGYIPLVGA PLGGAARALA
HGVRVLEDGV NYATGNLGCS FSIFLLALLS CLTIPASAY

FIGURE 1

MSTNPKPQRKTKRNTNRRPQDVKFPGGGQIVGGVYLLPRRGPRLGVRATRKTSERSQPR
GRRQPIPKARRPEGRTWAQPGYPWPLYGNEGCGWAGWLLSPRGSRPSWGPTDPRRRSR
NLGKVIDTLTCGFADLMGYIPLVGAPLGGAARALAHGVRVLEDGVNYATGNLPGCSFSI
FLLALLSCLTVPASA

COMBINATION HEPATITIS C VIRUS ANTIGEN AND ANTIBODY DETECTION METHOD

RELATED APPLICATION INFORMATION

This application claims priority to U.S. Patent Application No. 60/841,800 filed on Sep. 1, 2006, the content of which is herein incorporated by reference.

FIELD OF THE INVENTION

Among other things, the present invention relates to the field of viral detection and, in particular, to methods of detecting hepatitis C viral infections.

BACKGROUND OF THE INVENTION

Hepatitis C Virus (HCV) is now recognized as being the primary cause of transfusion-associated non A, non B NANB) hepatitis. HCV is a single stranded, positive sense RNA virus with similarities to flaviviruses and pestiviruses (Miller R H, and Purcell R. H. *Proc. Natl. Acad. Sci.* 87: 2057 (1991); Weiner A. J., et al., *Virology* 180: 842 (1990)) and is in global distribution. Although the acute presentation of HCV is generally mild, with only 25% of patients developing jaundice, a large proportion (>50%) of infected individuals go on to develop chronic hepatitis with serious and potentially life threatening sequelae such as cirrhosis and hepatocellular carcinoma (Jove J., et al., *Liver*, 8: 42 (1990); Hopf U., et al., *Hepatology*, 10: 69 (1990)).

Infection with HCV is currently diagnosed by direct detection of viral RNA by PCR or by detection of anti-HCV antibodies (generally to the HCV structural core protein or non-structural NS3 protein). In general it can take up to about 70 days after individual has been infected with HCV before the individual develops antibodies to the virus, therefore, antibody tests alone during this 70-day period cannot determine whether HCV infection has occurred. Viral RNA, on the other hand, can be detected about 10 days following infection, i.e. the "window period" for nucleic acid testing (NAT) is much shorter than for antibody testing. However, NAT tends to be less cost-effective than antibody testing and is prone to handling errors such as contamination. In addition, RNA levels can drop below the limit of detection for this nucleic acid testing when the initial peak of virus resolves, especially when testing pooled samples.

U.S. Pat. Nos. 6,596,476; 6,592,871; 6,183,949; 6,235,284; 6,780,967; 5,981,286; 5,910,404; 6,613,530; 6,709,828; 6,667,387; 6,007,982; 6,165,730; 6,649,735 and 6,576,417 describe antigens based on core protein and their use to detect HCV.

More recently, HCV antigen assays have been developed which demonstrate that HCV core protein antigens can be detected in a sample significantly sooner than antibodies can be detected. Studies have shown that the average time from the first viremic bleed to the first HCV antigen positive bleed is estimated at 2.0 days and that the average time to the first HCV antibody positive bleed at 50.8 days (Couroucé A. M., et al, *Transfusion*, 40, 1198-1202 (2000)).

A combination assay that detects HCV antigens and anti-HCV antibodies would, therefore, provide a means of detecting HCV infection within the above-noted 70-day window period, and would also identify exposure to HCV after seroconversion. An earlier diagnosis of HCV could help to prevent transmission of the virus from an infected individual to others individuals, and to minimize the risk of contamination of the blood supply. In order to develop a suitable combination assay, however, the problem of interference or cross-reactivity with respect to assaying an antigenic protein and antibodies to the same antigenic protein in a single assay must be addressed. Interference or cross-reactivity results when, for example, an HCV antigenic protein bound to a solid phase is used to capture anti-HCV antibodies in a sample. Because the HCV antigenic protein has the same epitopes as those recognized by the labeled antibody or antibodies used to detect the HCV antigenic protein in the sample, the labeled antibody or antibodies can also bind to the HCV antigenic protein on the solid phase thus giving a false positive response even in the absence of test sample.

Various combination assays to detect HCV infection have been described which use different strategies to overcome the problem of interference. International Patent Application No. PCT/US02/19958 (WO 03/002749) and U.S. Pat. Nos. 6,727,092 and 6,855,809 each describe a combination assay to detect HCV which uses monoclonal antibodies to detect core proteins from a sample, and core peptides or recombinant core proteins to capture antibodies to core proteins from a sample. The recombinant core proteins have been engineered such that the epitopes recognized by the monoclonal antibodies are eliminated or modified. In one example, the described combination assay uses a single peptide of 17 amino acid residues in length, corresponding to amino acids 11 to 28 of core protein to capture antibodies to core proteins from a sample. The preferred format, however, uses recombinant core proteins corresponding to amino acids 1 to 100 or 8 to 100 of the core protein sequence that have been engineered to delete the epitopes recognized by the monoclonal antibodies used in the assay.

International Patent Application No, PCT/FR03/01429 (WO 03/095968) and U.S. patent application Ser. No. 10/431,587 (US2004/0072267) describe another combination assay to detect HCV in which certain epitopes of the target antigens used to capture the antibodies are structurally modified and destroyed. The antibodies used in the assay are then specifically selected such that they precisely recognize the corresponding unmodified epitopes and thus cannot bind to the modified antigens, which no longer exhibit these same epitopes. A combination assay kit (MonoLisa® (HCV antigen-antibody Ultra, Bio-Rad Laboratories) based on this approach has been developed and has been determined to be an improvement over antibody-only based assays, but is still less sensitive than NAT (Ansaldi, F., et al., *J. Viral Hepatitis*, 13.5-10 (2006); Laperche, S., et al, *Transfusion*, 45:1965-1972 (2005); Laperche, S., et al., *J. Clin. Microbiol.*, 43:3877-3883 (2005)).

Similarly, US 2003/0108563 and US 2003/0152965 describe another combination assay in which the HCV core protein employed as antigen comprises a sequence in which amino acid residues other than the HCV core protein residues 10-43 are altered or deleted, and anti-HCV core antibodies are employed that do not recognize the modified HCV core protein.

This background information is provided for the purpose of making known information believed by the applicant to be of possible relevance to the present invention. No admission is necessarily intended, nor should be construed, that any of the preceding information constitutes prior art against the present invention.

All patents and publications referred to herein are hereby incorporated in their entirety by reference.

SUMMARY OF THE INVENTION

An object of the present invention is to provide a combination hepatitis C virus antigen and antibody detection method. In accordance with one aspect of the present invention, there is provided a method for detection of hepatitis C core protein and antibodies to hepatitis C core protein in a sample, the method preferably comprising the steps of: (a) contacting the sample with one or more capture peptides between about 4 and about 30 amino acid residues in length (optionally between about 12 and about 30amino acid residues in length) under conditions that allow formation of capture peptide:antibody complexes between the capture peptides and the antibodies to hepatitis C core protein, wherein each of the capture peptides preferably has an amino acid sequence comprising an epitope of hepatitis C core protein; (b) contacting the sample with a first antibody under conditions that allow formation of an antibody:antigen complex between the first antibody and the hepatitis C core protein, wherein the first antibody specifically binds the hepatitis C core protein at a first epitope which is different than the epitopes comprised by each of the one or more capture peptides; (c) detecting any capture peptide:antibody complexes formed in step (a) as a measure of the antibodies to the hepatitis C core protein, and (d) detecting any antibody:antigen complexes formed in step (b) as a measure of the hepatitis C core protein. In one embodiment, optionally each of the capture peptides comprises an epitope of hepatitis C core protein and an amino acid sequence selected from the group consisting of residues 16 to 30 of SEQ ID NO:1, residues 33 to 44 of SEQ ID NO:1, and residues 49 to 68 of SEQ ID NO:1, with any other amino acid residues present in the capture peptide being altered as compared to the sequence of SEQ ID NO:1).

In accordance with another aspect of the present invention, there is provided a kit for detection of hepatitis C core protein and antibodies to hepatitis C core protein in a sample, the kit preferably comprising: one or more peptides between about 4 and about 30 amino acids in length (optionally between about 12 and about 30 amino acid residues in length), preferably each of the peptides having an amino acid sequence comprising an epitope of hepatitis C core protein, and one or more antibodies, preferably wherein a first of the one or more antibodies is capable of specifically binding to a first epitope of hepatitis C core protein, wherein the first epitope is different than the epitopes comprised by the one or more capture peptides. In one embodiment, optionally each of the capture peptides comprises an epitope of hepatitis C core protein and an amino acid sequence selected from the group consisting of residues 16 to 30 of SEQ ID NO:1, residues 33 to 44 of SEQ ID NO: 1, and residues 49 to 68 of SEQ ID NO:1, with any other amino acid residues present in the capture peptide being altered as compared to the sequence of SEQ ID NO:1).

In accordance with another aspect of the present invention, there is provided a process for selecting reagents capable of simultaneously detecting an antigenic protein of a microorganism and antibodies to the antigenic protein, the reagents preferably consisting of one or more immunodominant peptides and one or more specific antibodies, the method preferably comprising the following steps: (i) providing a library of peptides, each of the peptides having an amino acid sequence corresponding to a portion of the amino acid sequence of the antigenic protein, wherein the amino acid sequences of the candidate peptides overlap; (ii) contacting the library of peptides with serum samples from subjects infected with the microorganism; (iii) contacting the library of peptides with negative control serum samples; (iv) selecting candidate peptides that bind to antibodies in a plurality of the serum samples in step (ii) and that do not bind to antibodies in the negative control serum samples in step (iii) to provide candidate peptides; (v) preparing immunodominant peptides comprising the sequence of one or more of the candidate peptides; (vi) contacting the immunodominant peptides with one or more candidate antibodies, and (vii) selecting one or more antibodies that do not bind to the immunodominant peptides to provide the specific antibodies.

In accordance with another aspect of the present invention, there is provided a kit for detection of an antigenic protein of a microorganism and an antibody to the antigenic protein in a sample, the kit preferably comprising: one or more specific antibodies capable of specifically binding to the antigenic protein and one or more immunodominant peptides derived from the amino acid sequence of the antigenic protein, the specific antibodies and the immunodominant peptides selected according to the process for selecting reagents of the present invention.

BRIEF DESCRIPTION OF THE DRAWINGS

These and other features of the invention will become more apparent in the following detailed description in which reference is made to the appended drawings.

FIG. 1 presents the amino acid sequence of HCV core protein [SEQ ID NO:1] used to generate immunodominant peptides in accordance with one embodiment of the present invention.

FIG. 2 presents the amino acid sequence of the HCV core protein p21c available from GenBank (Accession No. NP_751919) [SEQ ID NO:2].

FIG. 3 presents the sequences for a library of overlapping peptides derived from the sequence of HCV core protein [SEQ ID NOS:7 to 53], and illustrates the position of the immunogenic peptides SEQ ID NOS:3, 4, 5 and 54 (blue shaded area), as well as the epitopes for suitable antibodies (boxed sequences: GIVG [SEQ ID NO:6] and GPRLGVRA [SEQ ID NO:98]). Arbitrary numbers were applied for clarity of the figure; routinely numbering of the sequences identified in SEQ ID NOS:31-53 extends beyond residue 56.

FIG. 4 presents a schematic overview of a Process Control Monitoring procedure according to one embodiment of the invention.

FIG. 5 presents a schematic illustration of a combination assay in accordance with one embodiment of the invention.

FIGS. 6A and 6B depict the results of a comparison between the sensitivity of a combination assay in accordance with one embodiment of the invention (FIG. 6B) and the sensitivity of an alternative commercially available antibody/antigen assay (FIG. 6A).

DETAILED DESCRIPTION OF THE INVENTION

The present invention provides among other things an in vitro method that allows detection of hepatitis C by detecting hepatitis C virus (HCV) core protein and antibodies to HCV core protein (anti-core antibodies) in a single assay. The method preferably employs antibodies capable of specifically binding to core protein for detection of core protein in conjunction with selected immunodominant peptides for detecting anti-core antibodies. This method differs from the methods described previously that rely on construction of specialized fragments of core protein from which certain epitopes have been deleted or structurally modified in order to minimize the problem of cross-reactivity. In the method of the present invention, cross-reactivity preferably is limited or eliminated by utilizing short peptides, each of which has an amino acid sequence that corresponds to an immunodominant region of the native HCV core protein but which does not wholly encompass the epitope bound by the antibodies utilized in the method. Due to their relatively short length, the peptides used in the method of the present invention preferably can be synthesized more easily and with a higher degree of reliability (i.e. a lower error rate) than longer peptides.

Figure 4:
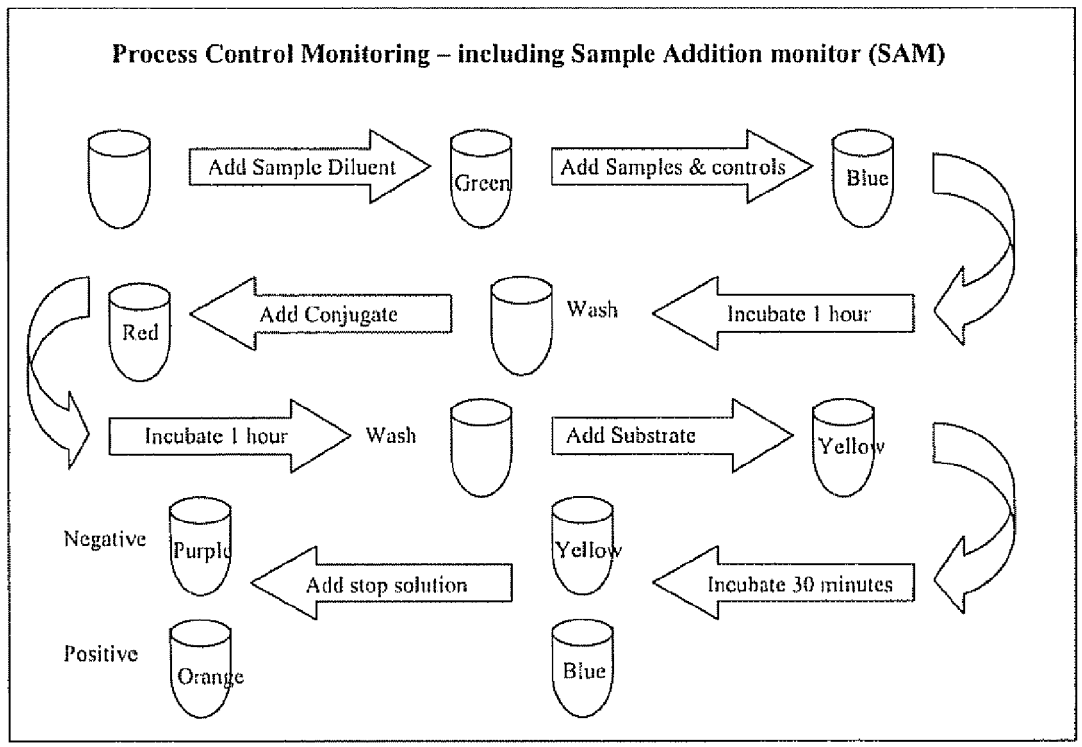

In addition, in one embodiment of the present invention, the use of a plurality of separate peptides, each comprising a different epitope, provides for adjustment of the ratio of epitopes being presented by adjusting the relative amounts of each peptide included in the method. Adjustment of the ratio of epitopes allows the sensitivity of the method to be optimized, without affecting specificity. In another embodiment of the present invention, the use of short peptide sequences corresponding to portions of the core protein in the above method preferably provides for an increased specificity compared to methods that use the entire core protein, or a longer fragment of core protein.

The present invention also provides for additional antibodies and/or antigenic proteins or peptides to be employed in the method for the detection of one or more HCV proteins or antibodies to HCV proteins other than core protein and antibodies to core protein. In one embodiment, the method of the present invention preferably utilizes an HCV non-structural protein or fragment thereof for detection of corresponding antibodies in addition to the immunodominant core protein peptides and antibodies to core protein.

The present invention further provides for kits for the detection of HCV comprising reagents for carrying out the method described above, i.e. the immunodominant core protein peptides and antibodies to core protein, and optionally provides additional antibodies and/or antigenic proteins or peptides for detection of one or more non-core HCV proteins.

The methods and kits of the present invention can be used, for example, to detect the presence of HCV in a subject, and/or to determine the suitability of donor blood or blood products for transfusion purposes.

Reagents suitable for use in the above-described methods and kits preferably are selected as described herein by identifying immunodominant peptides that contain key epitopes of the HCV core protein, selecting one or more of these immunodominant peptides for use in the method and/or kit, and selecting one or more anti-core antibodies that bind to an epitope other than the epitope present in the immunodominant peptide(s). It will be understood that this selection process can be broadly applied to the selection of reagents suitable for combination methods of detecting HCV antigenic proteins other than core protein and antibodies to same and, more generally, for combination methods of detecting antigenic proteins from other microorganisms and antibodies to these proteins. The present invention thus provides for a general process for screening reagents for the simultaneous detection of an antigenic protein and antibodies to the antigenic protein, the process comprising the steps of first identifying immunodominant peptides, each containing a key epitope recognized by antibodies present in the majority of subjects infected with the microorganism; selecting one or more of the identified immunodominant peptides; and identifying antibodies that recognize epitopes other than those contained in the selected peptides.

Definitions

Unless defined otherwise, all technical and scientific terms used herein have the same meaning as commonly understood by one of ordinary skill in the art to which this invention belongs.

The terms "corresponding to" or "corresponds to" as used herein in relation to an amino acid sequence indicates that the amino acid sequence is substantially identical to a reference amino acid sequence. By "substantially identical" it is meant that, when optimally aligned, for example using the methods described below, the amino acid sequence shares at least 70%, 75%, 80%, 85%, 90%, 95%, 96%, 97%, 98%, 99%, or 100% sequence identity with the reference amino acid sequence. Percent identity between two amino acid sequences is determined in various ways that are within the skill in the art, for instance, using publicly available computer software such as Smith Waterman Alignment (Smith, T. F. and M. S. Waterman, *J. Mol. Biol.* 147:195-7 (1981)); "BestFit" (Smith and Waterman, Advances in Applied Mathematics, 482-489 (1981)); BLAST program (Basic Local Alignment Search Tool; (Altschul, S. F., W. Gish, et al., *J. Mol. Biol.* 215: 403-10 (1990)) and variations and updates thereof; ALIGN, ALIGN-2, CLUSTAL, or Megalign (DNASTAR) software. In addition, those skilled in the art can determine appropriate parameters for measuring alignment, including algorithms needed to achieve maximal alignment over the length of the sequences being compared. In general, for peptides, the length of comparison sequences will be at least 10 amino acids, but one skilled in the art will understand that the actual length will depend on the overall length of the sequences being compared and may be at least 12, 15, 17, 18, 19 or 20 amino acids, or it may be the full-length of the peptide sequence.

The term "window period," as used herein, refers to the time from infection of an individual with hepatitis C virus until an assay can detect the infection.

The term "specifically binds" refers to the ability of individual antibodies to specifically react with an antigen. Binding specificity can be determined from the reference point of the ability of the antibody to differentially bind the specific antigen but not an unrelated antigen and, therefore, distinguish between two different antigens or, alternatively, from the reference point of the ability to differentially bind a specific epitope on an antigen but not other epitopes on the same antigen and, therefore, distinguish between two different epitopes.

The term "hepatitis C virus" or "HCV" includes all strains and all types, subtypes and genotypes of the virus responsible for hepatitis C.

As used herein, the term "about" refers to approximately a +/−10% variation from the stated value. It is to be understood that such a variation is always included in any given value provided herein, whether or not it is specifically referred to.

Naturally-occurring amino acids are identified throughout by the conventional three-letter or one-letter abbreviations indicated below, which are generally accepted in the peptide art and recommended by the IUPAC-IUB commission in biochemical nomenclature:

TABLE 1

Amino acid codes

| Name | 3-letter code | 1-letter code |
|---|---|---|
| Alanine | Ala | A |
| Arginine | Arg | R |
| Asparagine | Asn | N |
| Aspartic | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |

TABLE 1-continued

Amino acid codes

| Name | 3-letter code | 1-letter code |
| --- | --- | --- |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The peptide sequences set out herein are written according to the generally accepted convention whereby the N-terminal amino acid is on the left and the C-terminal amino acid is on the right.

1. Combination Method for Detection of HCV

One aspect of the present invention provides for a combination method for detection of HCV by detecting both HCV core protein and antibodies to core protein in a sample. The method preferably employs as reagents capture antibodies and capture peptides that have been selected to minimize or eliminate cross-reactivity. Methods of selecting these reagents are described below and are based on the identification and selection of immunodominant peptides of core protein, and the identification and selection of monoclonal antibodies that recognize epitopes other than those that are present on the selected immunodominant peptides. The present invention further includes methods of selecting such reagents.

According to the combination method of the present invention, a sample to be tested is contacted with one or more capture peptides, each comprising a different epitope of core protein, and with a capture antibody that is capable of specifically binding to HCV core protein at an epitope other than those present in the capture peptides Any capture peptide:antibody complexes and antibody:core protein complexes formed are then detected.

Capture peptide:antibody complexes and antibody:core protein complexes can be detected using appropriately labeled reagents as is known in the art Capture peptide:antibody complexes can be detected, for example, using a labeled core peptide ("detection peptide"), which can comprise the same sequence, or a sequence substantially identical to that of the capture peptide. Alternatively, the capture peptide:antibody complexes can be detected, for example, using a labeled secondary antibody, such as an anti-human antibody. Detection of capture peptide:antibody complexes in a "direct" format (i.e., using suitable detection peptides) may provide increased specificity over an "indirect" format employing a secondary antibody. Accordingly, in one embodiment, the method of the invention employs a direct format for the detection of the capture peptide:antibody complexes. Antibody:core protein complexes can be detected, for example, using a labeled secondary anti-core antibody, which can be the same or different than the capture antibody. The secondary anti-core antibody, however, should recognize an epitope other than those contained by the capture peptides and, when used, detection peptides.

Thus, in one embodiment, the combination method preferably comprises contacting a test sample with one or more capture peptides under conditions that allow the capture peptides to bind to anti-core antibodies in the sample to form capture peptide:antibody complexes. The sample preferably is simultaneously contacted with a capture antibody capable of specifically binding to HCV core protein under conditions that allow the capture antibody to bind to core protein in the sample to form antibody:core protein complexes. Cross-reactivity between capture of core protein and capture of antibodies to core protein is minimized or eliminated because the capture peptides do not contain the epitope of core protein that is recognized by the capture antibody. The method further preferably comprises detecting any antibody:core protein complexes and capture peptide:antibody complexes formed. In another embodiment, the capture peptides and capture antibody are immobilized on a solid surface.

In yet another embodiment, the method preferably employs more than one capture peptide, for example, two or more capture peptides, or three or more capture peptides.

The method further optionally comprises the step of simultaneously detecting a second antigenic protein of HCV or an antibody to a second antigenic protein of HCV. Thus, in one embodiment, a capture antigen that is capable of specifically binding to antibodies to the second antigenic protein of HCV, or a capture antibody capable of specifically binding to the second antigenic protein, can be included in the method. In another embodiment, the method further comprises the step of detecting any second antigenic protein:antibody complex using a labeled detection antigen or detection antibody that is capable of binding to the antibody or antigenic protein component of the second antigenic protein:antibody complex.

The method of the invention optionally can be in various formats known in the art, such as, for example, those described below. In one embodiment, the method is conducted as an immunoassay. For example, the capture peptides, capture antibodies (and capture antigen, when used) can be immobilized on a solid phase either directly or via presentation on a suitable carrier, while the detection peptides, detection antibodies (and detection antigens, when used) are provided in a liquid phase.

In another embodiment of the invention, the method preferably includes process control monitoring to ensure that the method is properly performed. Process control monitoring preferably includes sample addition controls and the use of color-coded reagents to ensure the integrity of the process. Other variations of process control monitoring would be apparent to one skilled in the art.

1.1. Core Protein Immunodominant Peptides

The capture peptides used in the combination method of the present invention are designed to specifically bind antibodies to HCV core protein. The peptides are immunodominant core protein peptides, i.e. peptides that comprise an amino acid sequence that corresponds to a portion of the native amino acid sequence of HCV core protein and contains one of the epitopes that are most commonly recognized by the immune system of individuals infected with HCV. The immunodominant peptides, therefore, preferably have an amino acid sequence that comprises at least one epitope that is recognized by antibodies to core protein found in samples from individuals at various stages of HCV infection.

In accordance with the present invention, the immunodominant peptides preferably are between about 4 and about 30 amino acid residues in length. In one embodiment, the peptides are between about 6 and about 30 amino acid residues in length, optionally between about 12 and about 30 amino acid residues in length. In a further embodiment, preferably the peptides are between about 6 and about 25 amino acid residues in length. In yet another embodiment, preferably the peptides are between about 8 and about 25 amino acid residues in length. In other embodiments, the peptides are preferably between about 10 and about 25 amino acid residues, between about 10 and about 22 amino acid residues, between about 12 and about 22 amino acid residues, and between about 12 and about 20 amino acid residues in length.

As noted above, the immunodominant peptides preferably comprise an amino acid sequence that corresponds to a portion of the native amino acid sequence of HCV core protein. An example of a HCV core protein sequence is provided in FIG. 1 [SEQ ID NO:1]. The amino acid sequence of the HCV core protein p21c also can be obtained from GenBank (Accession No. NP_751919) and is provided herein as FIG. 2 [SEQ ID NO:2]. Immunodominant peptide sequences can be identified from the core protein sequences by establishing those regions of core protein which are well conserved between the various genotypes of HCV and which are recognized by antibodies from the majority of subjects infected with HCV. In one embodiment, preferably a combination of immunodominant peptides is selected such that the epitopes comprised by the peptides bind antibodies from the major stages of infection. Suitable immunodominant peptides can be readily selected, for example, by following the process described herein (e.g., see Section 6 below). In one embodiment, preferably a plurality of immunodominant peptides are selected for use in the combination method such that each peptide comprises an epitope recognized by antibodies at different stages of infection, thus providing comprehensive coverage of the immune response to HCV.

In one embodiment, each immunodominant peptide preferably comprises at least 4 or at least 5 consecutive amino acids of the sequence as set forth in SEQ ID NO:1. In another embodiment, each of the peptides preferably comprises at least 4 or at least 5 consecutive amino acids of the sequence as set forth in amino acids 1-80 of SEQ ID NO:1 (i.e. the N-terminal region). In other embodiments, each immunodominant peptide preferably comprises at least 6, at least 7, at least 8, at least 10, or at least 12 consecutive amino acids of the sequence as set forth in SEQ ID NO:1.

In a specific embodiment, each of the peptides preferably comprises at least 4 or at least 5 consecutive amino acids of any one of the sequences: NRRPQDVKFPGGGQI [SEQ ID NO:3], GVYLLPRRGPRL [SEQ ID NO:4], TRKTSERSQPRGRRQPIPKA [SEQ ID NO:5], or NRRPQDVKFPGGGQIC [SEQ ID NO:54]. In another embodiment, each of the peptides comprises a sequence selected from: NRRP [SEQ ID NO:60], RRPQ [SEQ ID NO:61], RPQD [SEQ ID NO:62], PQDV [SEQ ID NO:63], QDVK [SEQ ID NO:64], DVKF [SEQ ID NO:65], VKFP [SEQ ID NO:66], KFPG [SEQ ID NO:67], FPGG [SEQ ID NO: 68], PGGG [SEQ ID NO:69], GGGQ [SEQ ID NO:70], GGQI [SEQ ID NO:71], GVYL [SEQ ID NO:72], VYLL [SEQ ID NO:73], YLLP [SEQ ID NO:74], LLPR [SEQ ID NO:75], LPRR [SEQ ID NO:76], PRRG [SEQ ID NO:77], RRGP [SEQ ID NO:78], RGPR [SEQ ID NO:79], GPRL [SEQ ID NO:80], TRKT [SEQ ID NO:81], RKTS [SEQ ID NO:82], KTSE [SEQ ID NO:83], TSER [SEQ ID NO:84], SERS [SEQ ID NO:85], ERSQ [SEQ ID NO:86], RSQP [SEQ ID NO:87], SQPR [SEQ ID NO:88], QPRG [SEQ ID NO:89], PRGR [SEQ ID NO:90], RGRR [SEQ ID NO:91], GRRQ [SEQ ID NO:92], RRQP [SEQ ID NO:93], RQPI [SEQ ID NO:94], QPIP [SEQ ID NO:95], PIPK [SEQ ID NO:96] and IPIKA [SEQ ID NO:97].

In another embodiment, each of the peptides preferably comprises at least 6 consecutive amino acids of any one of the sequences as set forth in SEQ ID NO:3, SEQ ID NO:4, SEQ ID NO:5, or SEQ ID NO:54. In another embodiment, each of the peptides preferably comprises at least 8 consecutive amino acids of any one of the sequences as set forth in SEQ ID NO:3, SEQ ID NO:4, SEQ ID NO:5, or SEQ ID NO:54. In other embodiments, each of the peptides preferably comprises at least 10 consecutive amino acids, at least 12 consecutive amino acids, or at least 14 consecutive amino acids of any one of the sequences as set forth in SEQ ID NO:3, SEQ ID NO:4, SEQ ID NO:5, or SEQ ID NO:54. In another embodiment, each of the capture peptides preferably comprises one of the sequences as set forth in SEQ ID NO:3, SEQ ID NO:4, SEQ ID NO:5, or SEQ ID NO:54.

In one embodiment, the present invention provides for immunodominant peptides that comprise a variant sequence of any one of SEQ ID NOs: 3, 4, 5, 54, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 or 90, wherein the variant sequence retains the ability to bind to antibodies to core protein found in samples from individuals at various stages of HCV infection. The term "variant" sequence, as used herein, refers to a peptide sequence in which one or more amino acid residue has been deleted, added or substituted in comparison to the reference peptide sequence. Preferably, when a variant sequence contains one or more amino acid substitutions they are "conservative" substitutions. A conservative substitution involves the replacement of one amino acid residue by another residue having similar side chain properties. As is known in the art, the twenty naturally occurring amino acids can be grouped according to the physicochemical properties of their side chains. Suitable groupings include alanine, valine, leucine, isoleucine, proline, methionine, phenylalanine and tryptophan (hydrophobic side chains); glycine, serine, threonine, cysteine, tyrosine, asparagine, and glutamine (polar, uncharged side chains); aspartic acid and glutamic acid (acidic side chains) and lysine, arginine and histidine (basic side chains). Another grouping of amino acids is phenylalanine, tryptophan, and tyrosine (aromatic side chains). A conservative substitution involves the substitution of an amino acid with another amino acid from the same group. In accordance with the present invention, a variant peptide comprises an amino acid sequence that is at least about 70% identical to the reference sequence. In one embodiment, the variant peptides comprise an amino acid sequence that is at least about 75% identical to the reference sequence. In other embodiments, the variant peptides comprise an amino acid sequence that is at least about 80%, at least about 85%, at least about 90%, or at least about 93% identical to the reference sequence.

The immunodominant peptides can comprise naturally occurring amino acids or optionally one or more non-naturally occurring amino acid. The non-naturally occurring amino acids are selected such that they do not interfere with the ability of the immunodominant peptide to bind to antibodies to core protein found in samples from individuals at various stages of HCV infection. Examples of non-naturally occurring amino acids include, but are not limited to, D-amino acids (i.e. an amino acid of an opposite chirality to the naturally occurring form), N-α-methyl amino acids, C-α-methyl amino acids, β-methyl amino acids, β-alanine (β-Ala), norvaline (Nva), norleucine (Nle), 4-aminobutyric acid (γ-Abu), 2-aminoisobutyric acid (Aib), 6-aminohexanoic acid (ε-Ahx), ornithine (orn), hydroxyproline (Hyp), sarcosine, citrulline, cysteic acid, cyclohexylalanine, α-amino isobutyric acid, t-butylglycine, t-butylalanine, 3-aminopropionic acid, 2,3-diaminopropionic acid (2,3-diaP), D- or L-phenylglycine, D- or L-2-naphthylalanine (2-Nal), 1,2,3,4-tetrahydroisoquinoline-3-carboxylic acid (Tic), D- or L-2-thienylalanine (Thi), D- or L-3-thienylalanine, D- or L-1-, 2-, 3- or 4-pyrenylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)- phenylalanine, D-p-fluorophenylalanine, D- or L-p-biphenylalanine D- or L-p-methoxybiphenylalanine, methionine sulphoxide (MSO) and homoarginine (Har). Other examples include D- or L-2-indole(alkyl)alanines and D- or L-alkylalanines, wherein alkyl is substituted or unsubstituted methyl, ethyl, propyl, hexyl, butyl, pentyl, isopropyl, iso-butyl, or iso-pentyl, and phosphono- or sulfated (e.g. —$SO_3H$) non-carboxylate amino acids.

The immunodominant peptides can comprise either naturally-occurring peptide bonds (i.e. —CONH—) or modified peptide bonds. The modified peptide bonds are selected such that they do not interfere with the ability of the immunodominant peptide to bind to antibodies to core protein found in samples from individuals at various stages of HCV infection. Examples of suitable modified peptide bonds are well known in the art and include, but are not limited to, —$CH_2NH$—, —$CH_2S$—, —$CH_2CH_2$—, —CH=CH— (cis or trans), —$COCH_2$—, —$CH(OH)CH_2$—, —$CH_2SO$—, —CS—NH— and —NH—CO— (i.e. a reversed peptide bond) (see, for example, Spatola, Vega Data Vol. 1, Issue 3, (1983); Spatola, in *Chemistry and Biochemistry of Amino Acids Peptides and Proteins*, Weinstein, ed., Marcel Dekker, New York, p. 267 (1983); Morley, J. S., *Trends Pharm. Sci.* pp. 463-468 (1980); Hudson et al, *Int J. Pept. Prot. Res.* 14:177-185 (1979); Spatola et al., *Life Sci.* 38:1243-1249 (1986); Hann, *J. Chem. Soc. Perkins Trans. I* 307-314 (1982); Almquist et al., *J. Med. Chem.* 23:1392-1398 (1980); Jennings-White et al., *Tetrahedron Lett.* 23:2533 (1982); Szelke et al., EP 45665 (1982); Holladay et al., *Tetrahedron Lett.* 24:4401-4404 (1983); and Hruby, *Life Sci* 31:189-199 (1982)). In one embodiment, the immunodominant peptides comprise one or more modified peptide bonds. When the immunodominant peptides comprises more than one modified peptide bonds, the modified peptide bonds can be the same or different.

The immunodominant peptides can be prepared by methods known in the art, such as, for example, chemical synthesis. Such methods include, but are not limited to, exclusive solid phase synthesis, partial solid phase synthesis, fragment condensation or classical solution synthesis (Merrifield, *J. Am. Chem. Soc*, 85:2149 (1963); Merrifield, *Science* 232:341 (1986)). Automated peptide synthesizers may also be used, such as, for example, the "9050 Plus Pep Synthesizer" from Millipore, the "Pioneer" synthesizer from Perseptive, the "433A" synthesizer from ABI (Applied Biosystems Inc.) or the "Symphony" synthesizer from Rainin. The peptides can also be prepared by homogeneous phase synthesis. The peptides can be purified using standard techniques such as chromatography (e.g., ion exchange, affinity, and sizing column chromatography or high performance liquid chromatography), centrifugation, differential solubility, or by other techniques familiar to a worker skilled in the art.

The ability of the immunodominant peptides to bind to antibodies to core protein found in samples from individuals at various stages of HCV infection can be easily determined by the skilled worker using commercially available seroconversion panels and standard methods including, but not limited to, those described herein.

It is contemplated that the immunodominant peptides employed in the combination method preferably may be immobilized on a suitable solid phase. The peptides can be immobilized using covalent or non-covalent (for example, ionic, hydrophobic, or the like) attachment to the solid phase, and further optionally may be modified to facilitate immobilization. Suitable modifications are known in the art and include the addition of a functional group or chemical moiety to either the C-terminus or the N-terminus of the peptide to facilitate cross-linking or attachment of the peptides to the solid support. Exemplary modifications include the addition of functional groups such as S-acetylmercaptosuccinic anhydride (SAMSA) or S-acetyl thioacetate (SATA), or addition of one or more cysteine residues to the N- or C-terminus of the peptide. Other cross-linking reagents are known in the art and many are commercially available (see, for example, catalogues from Pierce Chemical Co. and Sigma-Aldrich). Examples include, but are not limited to, diamines, such as 1,6-diaminohexane; dialdehydes, such as glutaraldehyde; bis-N-hydroxysuccinimide esters, such as ethylene glycol-bis(succinic acid N-hydroxysuccinimide ester), disuccinimidyl glutarate, disuccinimidyl suberate, and ethylene glycol-bis(succinimidylsuccinate); diisocyantes, such as hexamethylenediisocyanate; bis oxiranes, such as 1,4 butanediyl diglycidyl ether; dicarboxylic acids, such as succinyidisalicylate; 3-maleimidopropionic acid N-hydroxysuccinimide ester, and the like.

Other modifications include the addition of one or more amino acids at the N- or C-terminus, such as histidine residues to allow binding to $Ni^{2+}$ derivatized surfaces, of cysteine residues to allow disulfide bridge formation or binding to Sulfolink™ agarose. In one embodiment, one or more of the peptides preferably are modified by the addition of a cysteine residue. In another embodiment, one or more of the peptides preferably are modified by the addition of a functional group such as SAMSA. In a further embodiment, the peptide preferably comprises a N-terminal modification. In another embodiment, the peptide preferably comprises a C-terminal modification.

The present invention also provides that the peptide preferably may be modified to include one or more chemical spacers at the N-terminus or C-terminus in order to distance optimally the peptide sequences from the solid support. Spacers that can be used include but are not limited to 6-aminohexanoic acid; 1,3-diamino propane; 1,3-diamino ethane; and short amino acid sequences, such as polyglycine sequences, of 1 to 5 amino acids. In one embodiment, preferably one or more of the peptides include one or more 6-aminohexanoic acid spacers.

In an alternative embodiment, the peptides optionally can be conjugated to a carrier protein, such as bovine serum albumin (BSA), casein, or thyroglobulin, in order to immobilize them on a solid phase.

The invention also provides that the immunodominant peptides preferably can be used as detection peptides in the combination method of the present invention, in which case they can be modified to incorporate a detectable label. In one embodiment of the present invention, each of the one or more detection peptides preferably has an amino acid sequence that corresponds essentially to the amino acid sequence of one of the capture peptides. According to the invention, a detection peptide "corresponds essentially" to the amino acid sequence of one of the capture peptides when the detection peptide is identical or substantially identical in its amino acid sequence to the capture peptide, and also when some sequence variation is permitted such as replacement of an amino acid residue in the detection peptide with one that is substantially equivalent (e.g., a conservative amino acid substitution) and/or so as to result in a substantially equivalent functionality (e.g., ability to bind antibody). According to such a relationship, in one embodiment capture and detection peptides are employed in pairs with effectively the same amino acid sequence for solid phase and conjugate, but differing in spacers so as to optimize presentation for each particular role.

Detectable labels according to the invention preferably are molecules or moieties which can be detected directly or indirectly and are chosen such that conjugation of the detectable label to the detection peptide preferably does not interfere with the specific binding of anti-core antibodies in the test sample to the detection peptide. Methods of labeling peptides are well-known in the art and include, for example, the use of bifunctional cross-linkers, such as SAMSA (S-acetylmercaptosuccinic anhydride), to link the detection peptide to the detectable label. Other cross-linking reagents such as are known in the art or which similar to those described above likewise can be employed.

Detectable labels for use with the peptides of the present invention preferably include those that can be directly detected such as radioisotopes, fluorophores, chemiluminophores, enzymes, colloidal particles, fluorescent microparticles, and the like. The detectable label is either itself detectable or may be reacted with one or more additional compounds to generate a detectable product. Thus, one skilled in the art will understand that directly detectable labels of the invention may require additional components, such as substrates, triggering reagents, light, and the like to enable detection of the label. Examples of detectable labels include, but are not limited to, chromogens, radioisotopes (such as, e.g., $^{125}$I, $^{131}$I, $^{32}$P, $^{3}$H, $^{35}$S and $^{14}$C), fluorescent compounds (such as fluorescein, rhodamine, ruthenium tris bipyridyl and lanthanide chelate derivatives), chemiluminescent compounds (such as, e.g., acridinium and luminol), visible or fluorescent particles, nucleic acids, complexing agents, or catalysts such as enzymes (such as, e.g., alkaline phosphatase, acid phosphatase, horseradish peroxidase, β-galactosidase, β-lactamase, luciferase). In the case of enzyme use, addition of, e.g., a chromo-, fluoro-, or lumogenic substrate preferably results in generation of a detectable signal. Other detection systems such as time-resolved fluorescence, internal-reflection fluorescence, and Raman spectroscopy are optionally also useful.

The present invention also desirably provides for the use of labels that are detected indirectly. Indirectly detectable labels typically involve the use of an "affinity pair" i.e. two different molecules, where a first member of the pair is coupled to the detection peptide of the present invention, and the second member of the pair specifically binds to the first member. Binding between the two members of the pair is typically chemical or physical in nature. Examples of such binding pairs include, but are not limited to: antigens and antibodies; avidin/streptavidin and biotin; haptens and antibodies specific for haptens; complementary nucleotide sequences; enzyme cofactors/substrates and enzymes; and the like.

In one embodiment, preferably the detectable label is conjugated to the N-terminus of the detection peptide. In another embodiment, preferably the detectable label is conjugated to the C-terminus of the detection peptide. In some embodiments, optionally the detectable label is attached by a spacer to reduce potential steric hindrance, e.g., such as where a chemical spacer, including, but not limited to, 6-aminohexanoic acid, is used between the detection peptide sequences and the detectable label.

1.2 Anti-Core Antibodies

The antibodies used in the HCV detection method of the present invention preferably are antibodies that bind specifically to an epitope of HCV core protein other than the epitopes contained by the one or more immunodominant peptides selected for use in the method. In this context, "contained" means that the full-length sequence of the epitope is present in the peptide. One skilled in the art will appreciate that, in some embodiments, the peptides may comprise part of the sequence of an epitope bound by the antibody, without the epitope being functional to bind the antibody and thus antibodies that selectively bind to the full-length epitope would still be suitable for use in combination with the immunodominant peptide. Suitable antibodies can be selected, for example, from known and/or commercially available anti-core antibodies according to the epitope that they recognize and/or by following the process described herein (e.g., see Section 6 below).

The antibodies preferably are nonhuman antibodies, human antibodies or humanized antibodies. In one embodiment the antibodies preferably are human antibodies.

In one embodiment, the antibodies desirably are capable of binding to core protein as it exists in all or most genotypes of HCV. In another embodiment, the antibodies preferably are capable of capturing the antigenic protein from the 6 major genotypes of HCV (1, 2, 3, 4, 5 and 6), and their subtypes (as described in Stuyver et al., *PNAS USA*, 91:10134-10138 (1994); and Bukh, *Semin Liver Dis*, 15: 41-63 (1995)).

As used herein, the term "antibody" includes monoclonal antibodies and monospecific polyclonal antibodies, and both intact molecules as well as antibody fragments (such as, for example, Fab, Fab' and F(ab')2, Fd, single-chain Fvs (scFv), single-chain antibodies, disulfide-linked Fvs (sdFv) and fragments comprising either a VL or VH domain) which are capable of specifically binding to a core protein.

Polyclonal antibodies to a core-protein antigen can be produced by various procedures well known in the art. For example, the intact core protein or an antigenic polypeptide fragment thereof, which may be conjugated to a carrier protein, such as, e.g., an albumin, can be administered to a suitable host animal, such as a rabbit, mouse or rat, to induce the production of sera containing polyclonal antibodies specific for the core antigen. Various adjuvants known in the art can be used to increase the immunological response, depending on the host species, and include, but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

Monoclonal antibodies can be prepared using a wide variety of techniques known in the art including the use of hybridoma, recombinant, and phage display technologies, or a combination thereof. For example, monoclonal antibodies can be produced using hybridoma techniques such as those taught, for example, in Harlow et al. (*Antibodies: A Laboratory Manual*, Cold Spring Harbor Laboratory Press, 2nd ed. 1988); Hammerling, et al. (*Monoclonal Antibodies and T-Cell Hybridomas*, 563-681, Elsevier, N.Y., 1981). The term "monoclonal antibody," as used herein, however, is not limited to antibodies produced through hybridoma technology and refers generally to an antibody that is derived from a single clone, including a eukaryotic, prokaryotic, or phage clone, and is not limited by the method by which it is produced.

It will be appreciated that Fab and F(ab')2 and other antibody fragments optionally may be used in the HCV detection method of the present invention. Such fragments are typically produced by proteolytic cleavage, using enzymes such as papain (to produce Fab fragments) or pepsin (to produce F(ab')2 fragments). Alternatively, core protein-binding fragments can be produced through the application of recombinant DNA technology or through synthetic chemistry. For example, it is possible, to produce monoclonal antibodies by expression of a nucleic acid which has been cloned using a hybridoma. Single-chain Fvs can be produced by techniques such as those described in Huston et al., *Methods in Enzymol-*

*ogy* 203:46-88 (1991); Shu et al., *PNAS* 90:7995-7999 (1993); and Skerra et al., *Science* 240:1038-1040 (1988).

Monoclonal antibodies and antibody fragments also can be produced and screened by phage display and yeast display techniques. Examples of phage display methods that can be used to make the antibodies of the present invention include those disclosed in Brinkman et al., *J. Immunol. Methods* 182:41-50 (1995); Ames et al., *J. Immunol. Methods* 184:177-186 (1995); Kettleborough et al., *Eur. J. Immunol.* 24:952-958 (1994); Persic et al., *Gene* 187 9-18 (1997); and Burton et al., *Advances in Immunology* 57:191-280 (1994). Examples of yeast display methods that can be used to make and screen the antibodies of the present invention include those disclosed in International Application No. PCT/US2006/043608 (WO 2007/056507) (incorporated by reference for its teachings regarding same).

In one embodiment of the present invention, antibodies for use in the combination method preferably are those that specifically bind to epitopes of core protein other than those wholly comprised by SEQ ID NO:3, 4, 5 or 54. In another embodiment, the antibody is capable of binding to the epitope comprising the amino acid sequence QIVG [SEQ ID NO:6] or GPRLGVRA [SEQ ID NO:98].

The present invention also provides that the antibody preferably can be covalently or non-covalently attached to a solid phase. The antibody may, therefore, be modified to facilitate immobilization. Suitable modifications are known in the art and are described above with reference to the immunodominant peptides.

In one embodiment of the invention, anti-core antibodies preferably are used as detection antibodies to detect antibody:core protein complexes in the combination method of the present invention. In accordance with this embodiment, the anti-core antibodies can be modified to incorporate a detectable label, Suitable detectable labels are known in the art and are described above with reference to the immunodominant peptides. When both a capture and detection anti-core antibody are used in the method, preferably the antibodies are selected such that they recognize two different epitopes of core protein, neither of which are included in the sequence of the immunodominant peptides being employed.

1.3 Test Samples

Samples which may be tested according to the methods of the present invention include plasma, urine, whole blood, dried whole blood, serum, cerebrospinal fluid, saliva, tears, nasal washes or aqueous extracts of tissues and cells Suitable plasma samples include citrate plasma or EDTA plasma samples. Preferably such samples are isolated and testing is done in vitro. The test samples can be from any source, but preferably are human.

The sample may be tested directly or may be treated prior to testing. Treatments include the addition of components to the reaction that prevent hemolysis of the sample, procedures to ensure clotting of the sera prior to testing, or procedures to remove fibrin from the samples. Other treatments include treatment with a denaturing agent to promote disruption of the viral particle and/or exposure of the antigens. A variety of suitable denaturing agents are known in the art and include, for example, detergents, such as, Nonidet P-40 (NP40) (tert-octylphenoxy poly(oxyethylene) ethanol, also called IGEPAL CA630), Triton X-100, sodium dodecyl sulfate (SDS), and denaturants such as guanidine, urea, or an acid solution. Combinations of these reagents are also contemplated. In one embodiment, no sample pretreatment is required. In another embodiment, the sample is pretreated with one or more denaturing agents. In a further embodiment, the sample is pretreated with one or more denaturing agents selected from the group of: guanidine, urea and Triton X-100.

1.4 Other Antibodies/Antigens

It is contemplated that the method according to the present invention preferably may further comprise detection of one or more HCV antigenic proteins other than core protein, for example, the non-structural proteins NS3, NS4, and NS5, as well as E1 and/or E2 envelope structural proteins, or antibodies to one or more of these proteins. Antigenic proteins can be detected through the use of a capture antibody that specifically binds the protein, as is known in the art. Similarly, antibodies can be detected through use of a capture antigen, as is known in the art.

Suitable capture antigens of the invention preferably have an amino acid sequence corresponding to the HCV antigenic protein, or fragment thereof, and are capable of specifically binding antibodies to the HCV antigenic protein in a sample. In one embodiment, the method preferably employs a capture antigen to detect antibodies to a second antigenic protein in the test sample.

Suitable capture antibodies can be prepared using standard methods known in the art, including those described above. The capture antigen can also be prepared by standard techniques, for example, by recombinant methods or by purification from viral cultures. The present invention contemplates capture antigens that comprise an entire protein, fragments of a protein or one or more immunodominant peptides representing key epitopes of the protein. The capture antibody or antigen optionally may be immobilized on a solid phase.

The capture antibody:antigenic protein or capture antigen:antibody complexes formed when the respective capture molecule is brought into contact with the test sample can be detected by standard techniques, as described below.

In one embodiment, preferably a capture antigen is employed and detection of the capture antigen:antibody complexes is be achieved through the use of a detection antigen. Like the capture antigen, the detection antigen preferably has an amino acid sequence corresponding to the HCV antigenic protein, or fragment thereof, and is capable of specifically binding to the antibodies to the HCV antigenic protein from a sample. The detection antigen optionally can be conjugated to a detectable label, as described above in relation to the detection peptides, in order to determine the presence of the antibodies from the sample. In one embodiment, the detection antigen preferably is labeled by the conjugation method described in Example 2.

In one embodiment, the method according to the present invention employs an NS3 antigen to detect anti-NS3 antibodies in a sample. In another embodiment, the method employs recombinant NS3 protein. In a further embodiment, the method employs NS3 protein, or a fragment thereof, as capture antigen and for detection of any captured anti-NS3 antibodies. In a specific embodiment, the detection NS 3 protein is labeled by the conjugation method described in Example 2.

1.5 Detection of Antibody:Antigen Complexes

The various antibody:antigen complexes that are formed during the HCV detection method of the present invention (i.e. the capture peptide:antibody complexes, capture antibody:core protein complexes and, when applicable, capture antibody:second antigenic protein or capture antigen:antibody complexes) preferably are detected by standard techniques.

For example, detection of any capture peptide:antibody complexes can be achieved using a labeled secondary antibody, such as an anti-human antibody, capable of specifically binding to the captured antibody, or by using a labeled detection peptide having a sequence that is substantially identical to the sequence of the capture peptide. In one embodiment, in the combination method of the present invention, detecting any capture peptide:antibody complexes preferably is achieved through the use of one or more detection peptides, each of which has an amino acid sequence corresponding essentially to the amino acid sequence of one of the capture peptides. In a specific embodiment, one or more pairs of capture peptides/detection peptides preferably are used, in which the detection peptide has an amino acid sequence substantially identical to the sequence of its cognate capture peptide. Of course, the invention provides not only capture peptides/detection peptides where the sequence corresponds identically, but also where some sequence variation is permitted (e.g., with a substantially equivalent amino acid residue, and/or to result in a substantially equivalent functionality).

Detection of any antibody:core protein complexes can be achieved, for example, using a labeled detection antibody capable of specifically binding core protein at an epitope other than that recognized by the capture antibody. The epitope recognized by the detection antibody also preferably is absent from the one or more capture peptides, thus minimizing the occurrence of cross-reactivity in the method.

Detection of capture antibody:second antigenic protein or capture antigen:antibody complexes, when applicable, preferably can be achieved through the respective use of labeled detection antibodies, or a labeled version of the antigenic protein, or a fragment thereof. When detection antibodies are used, these should recognize an epitope of the second antigenic protein other than the epitope recognized by the capture antibody.

Depending on the label(s) employed, various standard detection techniques, for example, ELISA assays, radioimmunoassays, or other detection techniques, can be used to reveal the presence of the respective complexes formed. The same type or several types of labels can be used to detect the different types of complexes formed.

If desired, the detection of the presence of antigens and/or of antibodies in the test sample can be completed by quantification, for example by measuring the signals emitted by the labels (color, luminescence, radioactivity, etc.), according to the standard techniques known to those skilled in the art. Alternatively, the detection of the presence of HCV core protein or antibodies to core protein from a sample can be measured qualitatively.

2. Performance Characteristics of the Combination Method

The performance characteristics of the combination method, such as diagnostic sensitivity, diagnostic specificity and reproducibility, preferably can be assessed using standard techniques, such as those described below.

The combination method of the present invention preferably provides improved sensitivity over antibody-alone assays, while maintaining a high specificity, and thus optimally allows the window period to be closed relative to antibody-only testing. Diagnostic sensitivity and specificity of the combination method of the present invention can be assessed using standard techniques employing samples that contain HCV antigenic proteins and antibodies to antigenic proteins (positive controls), and suitable samples lacking such proteins and antibodies (negative controls). Such specimens or samples can be obtained from patients with acute hepatitis C infection or chronic hepatitis C infection. The methods also can be tested against commercially available seroconversion panels, such as, for example, those available from Boston Biomedica Inc. (BBI, West Bridgewater, Mass.), Bioclinical Partners (Franklin, Mass.) or North American Biologicals, Inc. (Boca Raton, Fla.). For example, suitable seroconversion panels available from BBI include, but are not limited to BBI (or PHV) 901, 904, 905, 906, 907, 908, 910, 911, 912, 913, 914, 915, 916, 917 and 919 Examples of suitable seroconversion panels that are available from Bioclinical Partners include, but are not limited to, BCP6211, BCP6213, BCP6222, BCP6225, BCP6227, BCP9041, BCP9054 and BCP9055. Examples of suitable seroconversion panels that are available from North American Biologicals include, but are not limited to, SC0010, SC0030, SC0040, SC00050, SC00060 SC00400, SC00402, SC00405 and SC00406. Suitable control negative samples include samples from uninfected subjects and/or from patients with conditions unrelated to hepatitis C infection, such as, pregnancy, autoimmune disease, or other acute viral infections, and samples from routine blood donors.

Diagnostic sensitivity is thus measured by using the method to test samples from patients with established hepatitis C infection, Diagnostic sensitivity measures the ability of the method to identify correctly samples that contain HCV antigenic proteins or antibodies to HCV antigenic proteins and is calculated as the number of true positive samples recognized by the method as positive, divided by the number of samples identified by a reference method as positive, expressed as a percentage Reference methods optionally include assays that measure only antibodies to HCV antigenic proteins, or nucleic acid testing (NAT) to measure HCV RNA. Because NAT is considered to be the "gold standard" for HCV testing, in one embodiment preferably sensitivity is measured against NAT as the reference method. In another embodiment, sensitivity is measured against one or; more seroconversion panels using NAT as the reference method.

In one embodiment, preferably the combination method according to the present invention has a diagnostic sensitivity for established hepatitis C infections of between about 90% and about 100% using NAT as the reference method. In yet another embodiment, preferably the combination method according to the present invention has a diagnostic sensitivity for established hepatitis C infections of between about 95% and about 100% using NAT as the reference method. In a further embodiment, preferably the combination method according to the present invention has a diagnostic sensitivity for established hepatitis C infections of between about 97% and about 99% using NAT as the reference method.

Diagnostic sensitivity also preferably is assessed by determining the ability of the method to detect early stage HCV infection (i.e. to close the window period). In one embodiment preferably the ability of the combination method according to the present invention to detect early phase of HCV infection is measured using commercially available seroconversion panels and compared to current "gold standard" methods that measure HCV RNA (NAT). In order to assess efficacy of detection, preferably the number of samples that yield a positive result using the method are determined and compared to the time of first detection of HCV infection as determined by NAT Any improvement of the combination method over other methods, such as antibody-only assays, also desirably can be assessed by comparing the results obtained with the combination method for the time of first detection of HCV infection with results obtained by the other method(s). In accordance with one embodiment of the present invention, preferably the combination method is capable of detecting HCV infection at an earlier stage of infection than antibody-only assays.

In one embodiment, the combination method according to the present invention preferably detects HCV infection between about 5 days and about 40 days earlier than methods that detect antibodies to HCV antigenic proteins only. In another embodiment, the combination method preferably detects HCV infection on average between about 10 days and about 30 days earlier than methods that detect antibodies to HCV antigenic proteins only. In a further embodiment, the combination method preferably detects HCV infection on average between about 12 days and about 30 days earlier than methods that detect antibodies to HCV antigenic proteins only. In another embodiment, the combination method preferably detects HCV infection on average between about 15 days and about 30 days earlier than methods that detect antibodies to HCV antigenic proteins only. In an alternate embodiment, the average delay in detection when compared to NAT methods preferably is between about 5 days and about 1 day. In another embodiment, the average delay in detection when compared to NAT methods preferably is between about 4 days and about 1 day. Average delay and the average difference between methods can be assessed, for example, by using a plurality of different samples from one or more seroconversion panels. For instance, optimally 10 or more samples, or desirably 20 or more samples.

Diagnostic sensitivity also can be assessed based on the lowest viral load the method is able to detect Viral loads of test samples can be assessed, for example, using quantitative NAT methods, such as those available commercially from Roche Diagnostics (e.g. AMPLICOR® HCV Monitor Test and COBAS AMPLICOR® HCV Monitor Test). In one embodiment of the present invention, the combination method preferably is capable of detecting viral loads of about $5\times10^4$ copies/mL and above. In another embodiment, the combination method preferably is capable of detecting viral loads of about $4\times10^4$ copies/mL and above. In a further embodiment, the combination method preferably is capable of detecting viral loads of about $3\times10^4$ copies/mL and above. In another embodiment, the combination method preferably is capable of detecting viral loads of about $2\times10^4$ copies/mL and above.

Diagnostic specificity of the method can be assessed, for example, by testing samples from various uninfected blood donors to determine the number of samples that yield a positive result. Diagnostic specificity is the ability of the method to identify correctly specimens that do not contain HCV antigenic proteins or antibodies to HCV antigenic proteins. An example of the specificity requirements for methods of testing HCV can be found in the Common Technical Specification for in vitro medical devices (2002/364/EC), which specifies a minimum requirement for screening assays of a specificity of 99.5% using a minimum of 5000 European donors or the equivalent. Diagnostic specificity can be calculated as the number of true negative specimens recognized by the method as being negative, divided by the number of specimens identified by a reference method as being negative, expressed as a percentage. Diagnostic specificity optionally also can be assessed by testing the method against potentially cross-reactive samples from patients with conditions unrelated to HCV infection. Such conditions include, for example, pregnancy, autoimmune disease, or other acute viral infections. In one embodiment of the invention, preferably the diagnostic specificity of the combination method according to the present invention is between about 95% and about 100%. In another embodiment, preferably the diagnostic specificity of the combination method is between about 96% and about 99%. In a further embodiment, preferably the diagnostic specificity of the combination method is between about 97% and about 99%.

The reproducibility of the method can be determined as is known in the art. For example, the method can be tested using replicates of multiple samples on separate occasions and determining the variation between the results obtained. The method also optionally can be tested using different preparations of reagents. Either intra-assay variation (variation within replicates of the same sample) and inter-assay variation (variation in testing on separate occasions), or both, can be measured using standard statistical methods as known in the art and represented by, for example, the coefficient of variation (or CV). In one embodiment, preferably the % CV of intra-assay variation of the method is less than about 10%, even more preferably from about 0.01% to about 10%. In another embodiment, preferably the % CV of inter-assay variation of the method is less than about 15%, even more preferably from about 0.01% to about 15%.

3. Assay Formats

The method according to the present invention desirably can be carried out in a variety of assay formats known in the art that are suitable for immunoassays, including but not limited to: in heterogeneous phase (such as solid phase) or in homogeneous phase; in one step or in two steps; as a sandwich-type assay; in a competitive or non-competitive format, and the like.

Exemplary immunoassay formats include, but are not limited to, microtiter plate assays, microsphere immunoassays, dual assay strip blots, rapid tests, Western blots, as well as the use of paramagnetic particles in, for example, an Architects assay (Frank Quinn, The Immunoassay Handbook, Second edition, edited by David Wild, pages 363-367, 2001). Such formats are known to those of ordinary skill in the art.

Other examples of format include an immunoassay format of the type sandwiched between two antibodies (capture and detection antibodies) which can be used for detecting the antigens present in the test sample, where the antibodies are revealed using either capture peptides or a capture antigen and a labeled conjugate which attaches to the antibody (according to a format commonly referred to as "indirect format"), for example labeled protein A or a labeled anti-immunoglobulin or anti-isotype antibody. The antibodies preferably can also be detected using a capture peptide and a labeled detection peptide which attach to the antibody (according to a format referred to as "antigen-antibody-antigen sandwich" or "double antigen sandwich"). Other modes of immunoassay can also be envisioned and are well known to those skilled in the art.

In one embodiment, preferably the method is conducted using a sandwich-based format. In another embodiment, preferably the core protein and the anti-core antibodies in the test sample are detected using an antibody sandwich and a double antigen sandwich, respectively.

For many of the above-noted immunoassay formats, optimally the immunodominant peptides and/or the anti-core antibodies are attached to a solid support. Examples of suitable solid supports include porous and non-porous materials, latex particles, magnetic particles, microparticles (see U.S. Pat. No. 5,705,330), beads, membranes, microtiter wells and plastic tubes. The choice of solid phase material can be determined based upon desired assay format performance characteristics and can be particulate (pellets, beads, and the like), or can be in the form of a continuous surface (membranes, meshes, plates, slides, disks, capillaries, hollow fibers, needles, pins, chips, solid fibers, gels, and the like). In one embodiment, preferably microplates or microtiter wells are used as the solid phase. Examples of suitable microplates or microtiter wells include those made of polystyrene, such as those marketed by the company Nunc, Denmark. In another embodiment, preferably solid particles or beads; or paramagnetic beads, such as those provided by Dynal or Merck-Eurolab (France) (Estapor™) may be used as the solid phase.

In yet another embodiment, preferably test tubes made of polystyrene or polypropylene, or the like, may be used as the solid phase.

Linking agents for covalent attachment are known in the art and may be part of the solid phase or the solid phase may be derivatized with reactive groups that allow attachment of the capture peptide and/or antibody via amino groups, carboxyl groups, sulfhydryl groups, hydroxyl groups and/or carbohydrate moieties. A variety of such cross-linking reagents is known in the art and many are commercially available (see, for example, S. S. Wong, ibid., and catalogues from Pierce Chemical Co. and Sigma-Aldrich). Examples include, but are not limited to, diamines, such as 1,6-diaminohexane; dialdehydes, such as glutaraldehyde; bis-N-hydroxysuccinimide esters, such as ethylene glycol-bis(succinic acid N-hydroxysuccinimide ester), disuccinimidyl glutarate, disuccinimidyl suberate, and ethylene glycol-bis(succinimidylsuccinate); diisocyantes, such as hexamethylenediisocyanate; bis oxiranes, such as 1,4 butanediyl diglycidyl ether; dicarboxylic acids, such as succinyidisalicylate; 3-maleimidopropionic acid N-hydroxysuccinimide ester, and the like. Various coupling chemistries known in the art optionally can be employed to immobilize the capture peptide and/or antibody on the solid support and include, for example, cyanogen bromide activation, N-hydroxysuccinimide activation, epoxide activation, sulfhydryl activation, hydrazide activation, and the use of carboxyl and amino derivatives for carbodiimide coupling chemistries.

Alternatively, as described above, preferably capture peptide and/or antibody are modified with a group that allows for attachment of the molecule to an appropriately modified solid support. For example, preferably the capture peptide and/or antibody comprise a His-tag that allows the peptide/protein to be immobilized on a solid support that has been modified to contain $Ni^{2+}$ ions. Similarly, preferably the capture peptide and/or antibody are modified with biotin and the support is modified to contain avidin/streptavidin. Other examples are known in the art.

One skilled in the art will appreciate that the method according to the present invention can be readily adapted for high-throughput screening of samples. High-throughput methods provide the advantage of processing a plurality of samples simultaneously and significantly decrease the time required to screen a large number of samples. The present invention, therefore, contemplates the use of high-throughput methods to simultaneously identify HCV antigenic proteins and antibodies to HCV antigenic proteins in samples.

For high-throughput screening, preferably reaction components are usually housed in a multi-container carrier or platform, such as a multi-well microtiter plate, which allows a plurality of reactions each containing a different test sample to be monitored simultaneously. The present invention also encompasses highly automated high-throughput screens to increase the efficiency of the screening process. Many high-throughput screening or assay systems are now available commercially, as are automation capabilities for many procedures such as sample and reagent pipetting, liquid dispensing, timed incubations, formatting samples into microarrays, microplate thermocycling and microplate readings in an appropriate detector, resulting in much faster throughput times.

4. Diagnostic Kits

The present invention further provides for diagnostic kits for the detection of HCV comprising reagents suitable for use in the combination method according to the present invention. Such reagents preferably include one or more capture antibodies capable of specifically binding to HCV core protein, and one or more capture peptides capable of binding to core protein according to the present invention. The reagents also optionally include one or more detection peptides for detecting HCV core protein, and one or more detection antibodies capable of specifically binding to HCV core protein.

The kit further preferably comprises a second antigenic protein (other than core), or a fragment thereof, for the capture of antibodies to the second antigenic protein, or antibodies to a second antigenic protein for capture of the second antigenic protein, and means to detect the captured antibodies or antigens, such as labeled antigenic protein or labeled antibodies, respectively. In one embodiment, preferably the kit comprises NS3 protein, or a fragment thereof, for detecting antibodies to NS3, and labeled NS3 protein, or a labeled fragment of NS3 protein for detecting the captured antibodies.

The detection reagents provided in the kit preferably incorporate a detectable label, such as a fluorophore, radioactive moiety, enzyme, biotin/avidin label, chromophore, chemiluminescent label, or the like, or the kit optionally includes the necessary components for labeling the reagents. The reagents can be provided in separate containers, or pre-dispensed into or immobilized in an appropriate assay format. For example, the capture reagents can be provided immobilized on a suitable solid support, such as a microtiter plate or wells, and the detection reagents can be provided in suitable separate containers.

The kits optionally include reagents required to conduct a diagnostic assay, such as buffers, salts, enzymes, enzyme co-factors, substrates, detection reagents, washing reagents, and the like. Other components, such as buffers and solutions for the isolation and/or treatment of a test sample, may also be included in the kit. The kit may additionally include one or more controls. One or more of the components of the kit may be lyophilized, and, if so, the kit may further comprise reagents suitable for the reconstitution of the lyophilised components.

The various components of the kit desirably are provided in suitable containers. As indicated above, preferably one or more of the containers may be a microtiter plate. Where appropriate, the kit also optionally contains reaction vessels, mixing vessels and other components that facilitate the preparation of reagents or the test sample. The kit may also include one or more instrument for assisting with obtaining a test sample or measuring/dispensing reagents, such as a syringe, pipette, forceps, measured spoon, measured container, or the like.

In one embodiment, preferably the kit comprises reagents for process control monitoring, for example, sample addition controls, and/or color-coded reagents. An example of process control monitoring according to one embodiment of the invention is shown in FIG. 4. Addition of the various components of the assay to the wells may be confirmed by examining the plate for specific colours as shown in FIG. 4. For example, if reagents are color-coded, then the addition of one reagent to another in a particular step preferably results in a change in the color of the mixture, thus providing an indication that the step was carried out. Alternatively, the optical density of the solution in a well may be monitored to determine whether the steps of the method were carried out. Reagents can be provided for process control monitoring of one, or more than one, of the steps of the combination method.

The kit also optionally includes instructions for use, which may be provided in paper form or in computer-readable form, such as a disc, CD, DVD or the like. The kit may also comprise computer readable media comprising software that assists in the interpretation of results obtained by the combination methods. Other variations of the kit components would be known to one of skill in the art.

5. Uses of the Combination Methods and Diagnostic Kits

The combination method and diagnostic kits according to the present invention preferably are used for various diagnostic purposes. Such diagnostic purposes include but are not limited to detection of initial infection with HCV, monitoring a patient's response to a therapeutic drug, detection of re-infection with HCV, determination of viral load, and determination of presence and status of infection (acute vs. chronic).

The combination method and diagnostic kits preferably are also used for non-diagnostic purposes, such as, e.g., genotyping assays, or detection of HCV mutants or multiple serovars. The present invention also encompasses the use of the combination method and diagnostic kits for detection of HCV within a pool of blood samples or blood products, such as donor blood. In this context, high-throughput screening according to the method of the instant invention can be useful to facilitate large-scale screening, such as screening large population sizes for epidemiological studies or screening blood banks or organs for samples contaminated with HCV.

Of course, it goes without saying that any of the exemplary formats herein, and any assay or kit according to the invention can be adapted or optimized for use in automated and semi-automated systems (including those in which there is a solid phase comprising a microparticle), as described, e.g., in U.S. Pat. Nos. 5,089,424 and 5,006,309, and as, e.g., commercially marketed by Abbott Laboratories (Abbott Park, Ill.) including but not limited to Abbott's ARCHITECT®, AxSYM, IMX, PRISM, and Quantum II platforms, as well as other platforms.

Additionally, the assays and kits of the present invention optionally can be adapted or optimized for point of care assay systems, including Abbott's Point of Care (i-STAT™) electrochemical immunoassay system. Immunosensors and methods of manufacturing and operating them in single-use test devices are described, for example in U.S. Pat. No. 5,063, 081 and published US Patent Applications 20030170881, 20040018577, 20050054078, and 20060160164 (incorporated by reference herein for their teachings regarding same).

6. Process for Selecting Reagents for Combination Assays

The present invention also provides for a process for selecting reagents suitable for use in combination methods, such as the combination method for HCV detection described herein. The selection process preferably allows reagents to be selected such that there is little, if any, cross-reactivity between reagents used to capture and detect an antigenic protein of a microorganism (e.g., bacterium, parasite, fungus or virus), and reagents for capturing and detecting antibodies to the antigenic protein when these reagents are used together. Reagents suitable for capturing or detecting an antigenic protein include antibodies, and reagents suitable for capturing or detecting antibodies to the same antigenic protein include immunodominant peptides.

In one embodiment, the process is applied to selection of reagents to detect HCV core protein. It will be understood, however, that this selection process can be broadly applied to the selection of reagents suitable for combination methods of detecting HCV antigenic proteins other than core protein and antibodies to same and, more generally, for combination methods of detecting antigenic proteins from other microorganisms and antibodies to these proteins. In one embodiment, the method is applied to selection of reagents to detect a viral protein. In other embodiments, the method is applied to the selection of reagents to detect an antigenic protein from human immunodeficiency virus (HIV), for example, p24.

The selection process preferably comprises the steps of selecting an antigenic protein of a microorganism of interest; identifying immunodominant peptides for the antigenic protein, each immunodominant peptide containing a key epitope recognized by antibodies present in the majority of subjects infected with the microorganism at a range of infection stages; selecting one or more of the identified immunodominant peptides, and identifying antibodies that recognize epitopes other than those contained in the selected peptides.

One or more immunodominant peptides preferably are identified by establishing the immunodominant regions of the antigenic protein which are well conserved between the various genotypes of the microorganism and contain key epitopes of the antigenic protein recognized by antibodies present in the majority of individuals infected with the microorganism, including different seroconversion samples and late stage samples reactive to the antigenic protein. Thus the immunodominant peptides preferably have an amino acid sequence that corresponds to the amino acid sequence of a fragment of the antigenic protein.

In order to select one or more immunodominant peptides according to the present invention, preferably the amino acid sequence of the antigenic protein is first obtained. If the amino acid sequence of the antigenic protein is known in the art the amino acid sequence can be obtained from various publicly available databases such as GenBank™ or from publications or journal articles. Alternatively, if the amino acid sequence of the antigenic protein is unknown, for example, if the antigenic protein is a novel protein, the amino acid sequence of the antigenic protein can be obtained as is known in the art. For example, protein or peptide sequencing techniques, such as Edman degradation or mass spectrometry may be used, or the DNA encoding the protein can be cloned and sequenced. If the DNA sequence of the antigenic protein is known, the amino acid sequence of the antigenic protein may be deduced from the DNA sequence.

Once the amino acid sequence of the antigenic protein is obtained, preferably a library of peptides is prepared. Each peptide in the library has an amino acid sequence corresponding to a fragment of the amino acid sequence of the antigenic protein. The length of the peptides is selected to be long enough such that the total size of the library remains manageable, and short enough to minimize the occurrence of multiple epitopes being present in a single peptide. In general peptides of between about 5 and about 20 amino acids in length are suitable. In one embodiment, preferably the peptides are between about 7 and about 20 amino acids n length. In another embodiment, preferably the peptides are between about 8 and about 20 amino acids in length. In a further embodiment, preferably the peptides are between about 10 and about 20 amino acids in length, optionally between about 12 and about 20 amino acids in length. In other embodiments, preferably the peptides are between about 8 and about 18 amino acids, between about 8 and about 16 amino acids, between about 10 and about 18 amino acids, between about 10 and about 16 amino acids, and between about 10 and about 14 amino acids in length.

The peptides are also designed such that their amino acid sequences preferably overlap by at least 2 amino acids. Overlaps of between about 3 and about 14 amino acids are also contemplated. The selected overlap for the peptides will be dependent on the resolution required for the library as well as the length of the peptides comprised by the library. In general, the overlap is equal to or less than two-thirds of the length of the peptide. Such selection of overlap to obtain desired library characteristics is well within the ordinary skill and knowledge of one working in this field. Methods of preparing libraries of peptides likewise are known in the art.

Candidate immunodominant peptides can be identified from the library of peptides as follows and as illustrated in Example 1. Each peptide from the library of peptides preferably is tested against a plurality of samples from subjects infected with the microorganism, and potential peptides are selected by identifying those that bind to antibodies in the majority of the samples, including samples from different stages of infection.

The peptides preferably are also screened against uninfected samples, including those that are known to result in a false positive result for infection by the microorganism. These false-positive samples are negative control samples that identify cross-reactive areas in the peptide sequences. Peptides that react with the negative control samples (i.e. contain cross-reactive areas) preferably are avoided. Peptides that bind to antibodies in a plurality of samples from subjects infected with the microorganism, but that do not contain cross-reactive areas that result in a false-positive signal desirably are selected as candidate immunodominant peptides.

The immunodominant peptides are then prepared based on the sequences of the candidate immunodominant peptides identified as described above. The immunodominant peptides preferably comprise the sequence of at least one candidate peptide, and also optionally comprise part or all of the sequence of one or both of the two peptides immediately flanking the candidate peptide provided that these flanking peptides do not comprise cross-reactive areas.

One or more antibodies are next selected based on their ability to efficiently capture the antigenic protein and to bind to an epitope other than those wholly contained by the selected immunodominant peptides. As noted above, in one embodiment, it is contemplated that an immunodominant peptide comprises part of the sequence of an epitope bound by the selected antibody, as the partial epitope will not be functional to bind the antibody. In one embodiment, preferably antibodies are selected that bind to the form or forms of the antigenic protein that occur in all or most genotypes of the microorganism (if there are multiple genotypes of the microorganism).

Suitable antibodies can be selected from commercially available antibodies, or alternately, a library of antibodies capable of specifically binding to the antigenic protein can be prepared. Methods of preparing such libraries are known in the art. The epitopes that are recognized by the antibodies can then be mapped, if necessary, using art known methods. For example, the antibodies can be screened against the library of peptides from which the immunodominant peptides were selected. For some commercially available antibodies, the epitope to which the antibody binds is already known thus eliminating the need for the mapping step. Once appropriate antibodies have been selected, preferably they are screened against the selected immunodominant peptides to ensure that they do not cross-react with the epitopes comprised by the peptides.

Once immunodominant peptides have been identified, and the epitopes recognized the monoclonal antibodies have been determined, combinations of immunodominant peptides and monoclonal antibodies that do not bind to the immunodominant peptides preferably are selected for use in combination assays Selected immunodominant peptides can be used as capture and detection peptides, and selected monoclonal antibodies preferably are used as capture and detection antibodies.

The invention will now be described with reference to specific examples. It will be understood that the following examples are intended to describe illustrative embodiments of the invention and are not intended to limit the invention in any way.

EXAMPLES

Example 1

Selection of Immunodominant Core Peptides and Anti-Core Antibodies

Figure 3:
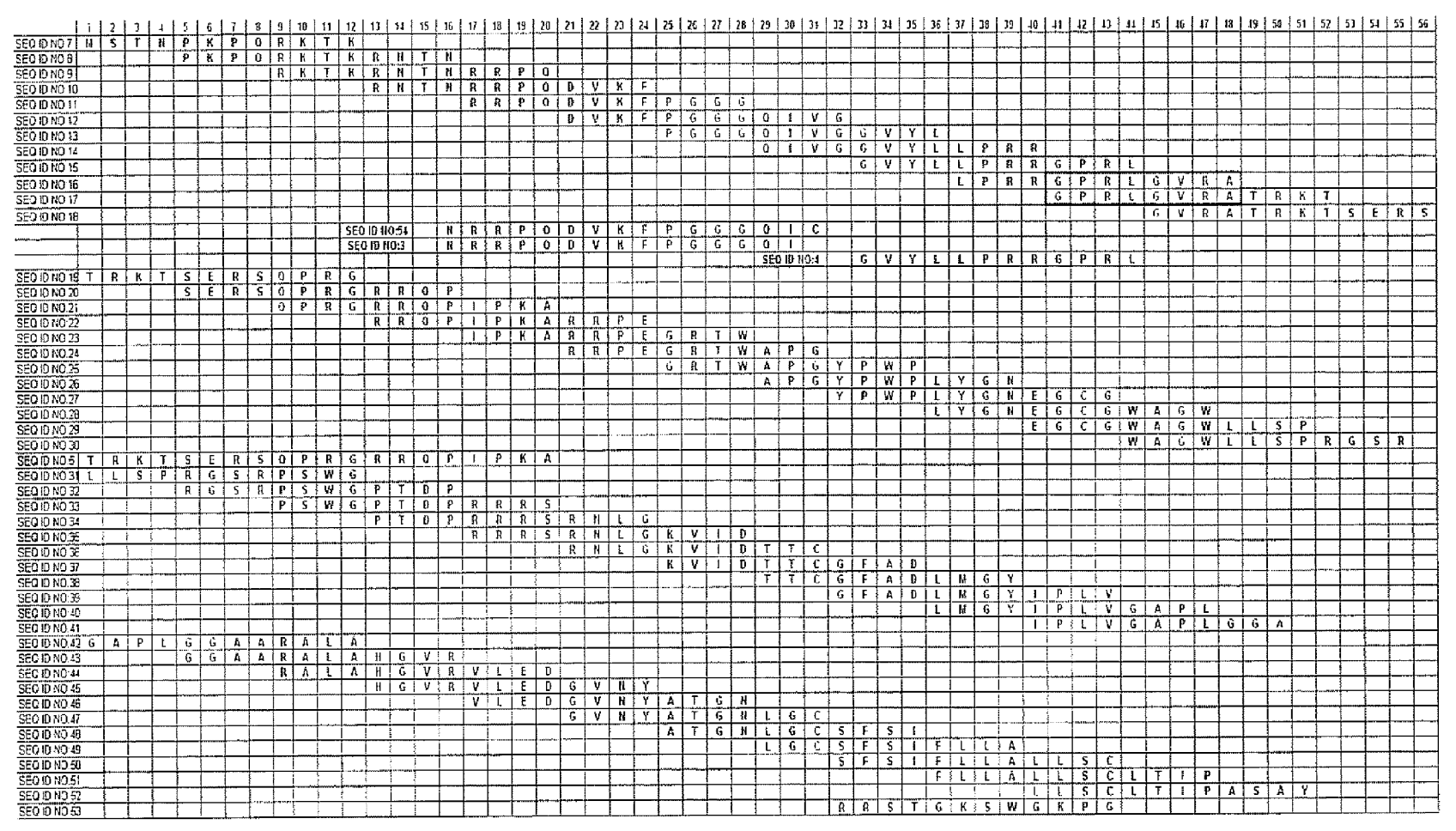

A series of peptides (SEQ ID NOS:7-53) were prepared that represent overlapping fragments of core protein. Each peptide was 12 amino acids in length and overlapped with the preceding (N-terminal) peptide by 8 amino acids and the subsequent (C-terminal) peptide by 8 amino acids (see FIG. 3). These peptides were conjugated to BSA and coated onto microtiter plates and screened against real human positive sera in an anti-human format to map the key antigenic regions of the protein. The same plates were used in an anti-mouse format to identify the binding sites of selected monoclonal antibodies used.

The following immunodominant peptides were prepared based on the results of this screening process.

```
Core capture peptide 1:
NRRPQDVKFPGGGQIC.                    [SEQ ID NO: 54]
```

Core capture peptide 1 has an amino acid sequence corresponding to residues 16 to 30 of the core protein sequence shown in FIG. 1 [SEQ ID NO:1] and is modified by the addition of a cysteine residue to the C-terminus of the peptide.

```
Core capture peptide 2:
SAMSA-GVYLLPRRGPRL.                  [SEQ ID NO: 55]
```

Core capture peptide 2 has an amino acid sequence corresponding to residues 33 to 44 of the core protein sequence shown in FIG. 1 [SEQ ID NO:1] and is modified by the addition of a SAMSA functional group to the N-terminus of the peptide.

```
Core capture peptide 3:
                                     [SEQ ID NO: 56]
SAMSA-Ahx-Ahx-Ahx-TRKTSERSQPRGRRQPIPKA.
```

Core capture peptide 3 has an amino acid sequence corresponding to residues 49 to 68 of the core protein sequence shown in FIG. 1 [SEQ ID NO:1] and is modified by the addition of a SAMSA functional group and three aminohexanoic acid (Ahx) spacers to the N-terminus of the peptide.

```
Core detection peptide 1:
SAMSA-Ahx-NRRPQDVKFPGGGQI.           [SEQ ID NO: 57]
```

Core detection peptide 1 has an amino acid sequence corresponding to residues 16 to 30 of the core protein sequence shown in FIG. 1 [SEQ ID NO:1] and is modified by the addition of a SAMSA functional group and an Ahx spacer to the N-terminus of the peptide.

```
Core detection peptide 2:
SAMSA-Ahx-Ahx-Ahx-GVYLLPRRGPRL.      [SEQ ID NO: 58]
```

Core detection peptide 2 has an amino acid sequence corresponding to residues 33 to 44 of the core protein sequence shown in FIG. 1 [SEQ ID NO:1] and is modified by the addition of a SAMSA functional group and three Ahx spacers to the N-terminus of the peptide.

```
Core detection peptide 3:
SAMSA-Ahx-TRKTSERSQPRGRRQPIPKA.      [SEQ ID NO: 59]
```

Core detection peptide 3 has an amino acid sequence corresponding to residues 49 to 68 of the core protein sequence shown in FIG. 1 [SEQ ID NO:1] and is modified by the addition of a SAMSA functional group and an Ahx spacer to the N-terminus of the peptide.

All three detection peptides were conjugated to horseradish peroxidase through the SAMSA moiety.

Monoclonal antibodies to be used in combination with the above capture and detection peptides were selected that bind to epitopes other than those comprised wholly by the peptides.

Monoclonal #1 (KTM163): binds to the epitope QIVG [SEQ ID NO:6] defined by residues 29 to 32 of the core protein sequence shown in FIG. 1 [SEQ ID NO:1].

Monoclonal #2 (KTM145): binds to the epitope GPRLGVRA [SEQ ID NO:98] defined by residues 41 to 48 of the core protein sequence shown in FIG. 1 [SEQ ID NO:1].

Monoclonal antibody #1 (KTM163) was conjugated to horseradish peroxidase and used as a detection antibody, and monoclonal antibody #2 (KTM145) was used as a capture antibody.

Monoclonal antibodies KTM163 and KTM145 were obtained from Kyowa Hakko Kogyo Co., Ltd., Japan. (Other monoclonal antibodies having the binding properties of KTM145 and KTM163 may also be utilized for purposes of the present invention.)

Example 2

Preparation and Labeling of Recombinant NS3 Antigen

A conjugate of recombinant hepatitis C virus (HCV) non-structural protein NS3 and horseradish peroxidase (HRP) was prepared as follows. This method is the subject of a patent application entitled "Antigenic Protein Conjugates and Process for Preparing Same", filed Sep. 1, 2006 as U.S. Patent Application No. 60/841,801 (incorporated by reference for its teachings regarding same).

The recombinant NS3 (rNS3) was prepared according to standard protein expression methods and comprised the native sequence of NS3 together with a leader sequence from the vector at a position N-terminal to the native sequence.

An HRP-maleimide solution was prepared as follows, A 2-fold molar excess of sulpho-SMCC was dissolved in DMSO (Pierce) and added to 100 mg/mL HRP dissolved in 25 mM HEPES/1 mM EDTA, pH 7.8. The solution was swirled gently and left for 45 minutes at room temperature. The HRP-maleimide was purified by gel filtration by loading the solution (2.5 mL) on a PD10 column (Pharmacia) and eluting with 25 mM HEPES/1 mM EDTA, pH 6.8 (3.2 mL).

The rNS3 was reduced in an aqueous solution of TCEP (Perbio or Calbiochem) containing a 10-fold excess of TCEP, at a pH of 6.8 for 2 hours at room temperature to provide the reduced rNS3. Ten molar equivalents of horseradish peroxidase (HRP)-maleimide, prepared as described above, were added to the solution of reduced rNS3 and TCEP, and the resulting mixture was swirled and left to stand for 16-24 hours at 2-8° C. to produce rNS3-HRP. Any unreacted sulfhydryl groups were then blocked by reaction with an excess of iodoacetic acid for 3 hours at room temperature. The resulting blocked rNS3-HRP was purified by gel filtration on a PD10 column (Sephadex™ G-25 Medium; GE Healthcare Bio-Sciences AB, Uppsala, Sweden) by loading 2.5 mL of product onto each column and eluting in 3 mL provide the final rNS3-HRP product. The total time required to carry out the four-step procedure to prepare the final rNS3-HRP product was 1½ days. In contrast, rNS3-HRP prepared by conventional methods required nine steps (including purification of intermediate products) and took a total time of 3 days.

A comparison of the ability of the rNS3 conjugate prepared by the above "in situ" method and an rNS3 conjugate prepared by the nine step conventional method to detect anti-HCV antibodies indicated that the in situ rNS3-HRP conjugate can be used at a higher titer (i.e. lower concentration) than the conventional rNS3-HRP and gave a higher signal and a lower negative. In addition, the rNS3-HRP conjugate can be used in the absence of DTT or TCEP, whereas for the rNS3-HRP conjugate prepared according to the conventional method, 6 mM DTT had to be added to the conjugate diluent. If the conventional rNS3-HRP was used without DTT or TCEP, the positive signal was substantially diminished. These results suggest that the in situ method holds the protein structure in an open confirmation, and rather than the bulky HRP moiety masking key epitopes, as may be expected, they are revealed in a stable manner.

Example 3

Immunoassay Immunoassay Kit for Hepatitis C Virus Detection

Figure 5:
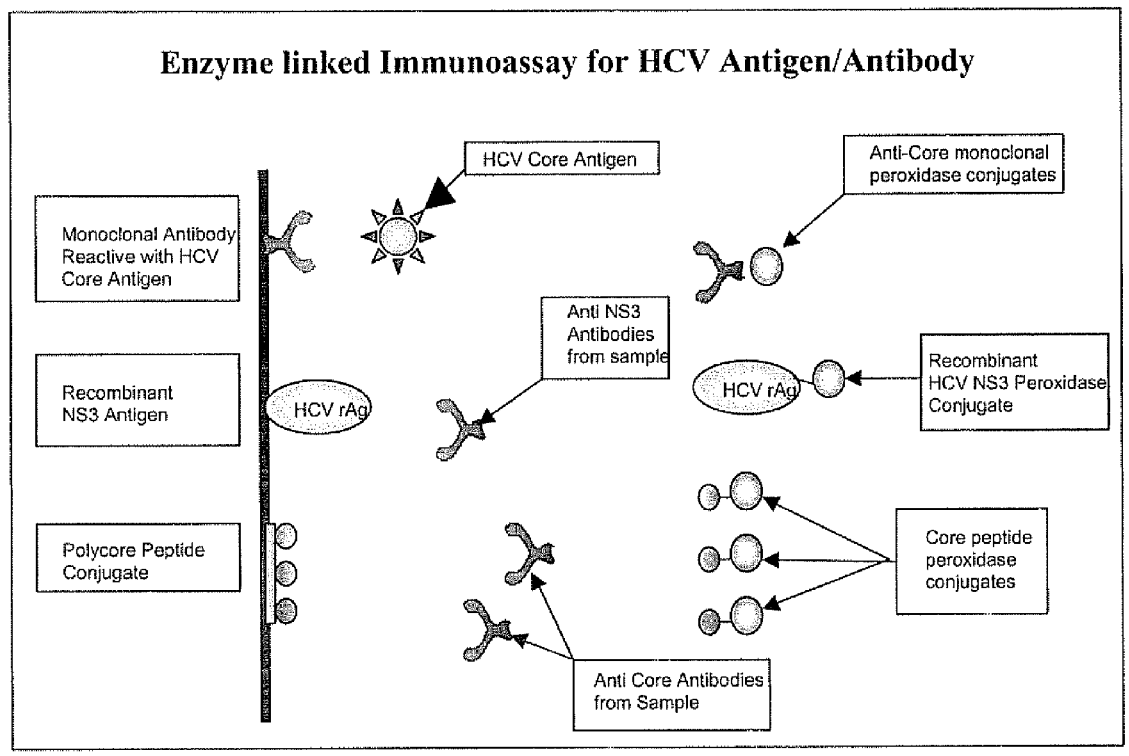

This example describes an exemplary immunoassay kit containing reagents that are suitable for use in the combination method of the present invention and their preparation for use. The immunoassay kit comprises the immunodominant peptides and monoclonal antibodies described in Example 1 and the recombinant NS3 antigen described in Example 2. The format of the assay conducted using the kit is shown schematically in FIG. 5. The "polycore peptide conjugate" shown in FIG. 5 comprises the three core peptides conjugated to bovine serum albumin (BSA) to improve binding and presentation of the peptides on the solid surface. Appropriate storage conditions for all reagents are 2 to 8° C., unless otherwise stated.

1. Coated Wells

The kit includes coated wells (e.g., microtiter plates) which a restored in a foil bag. One plate or five plates, each plate of 96 wells, is coated with purified recombinant HCV NS3 antigen, peptides (SEQ ID NOs: and anti-HCV core monoclonal antibody. The wells are allowed to reach 18 to 30° C. before removing them from the bag. Care is taken not to cut the foil bag close to the end seal. If less than the whole plate was being used, unused wells were placed with the desiccant in the foil bag, carefully sealed with tape and returned to 2 to 8° C. for up to 3 months.

2. Sample Diluent

The kit includes one bottle or two bottles containing 18 mL of sample diluent having the chemical composition shown in Table 2.

TABLE 2

Chemical Composition of the Sample Diluent

| CAS Number | Chemical/Biological Substance Name | Wt/Wt % |
| --- | --- | --- |
| 7365-45-9 | Hepes | 0.220% |
| 9002-93-1 | Triton-X-100 | 3.925% |
| 3458-28-4 | Mannose | 9.259% |
| 50-01-1 | Guanidine | 3.537% |
| 57-13-6 | Urea | 2.224% |
| 7647-14-5 | Sodium Chloride | 2.164% |
| 115-40-2 | Bromocresol Purple (Sodium Salt) | 0.018% |
| 910010-01-6 | Filtered Heated Calf Serum | 4.630% |
| 1186 | Sodium Alkyl Paraben (Nipasept)* | 0.317% |
| 990001-12-8 | A56620 | 0.925% |
| 910010-14-0 | HB05 Post Protein G | 0.557% |
| 6381-92-6 | EDTA | 1.850% |
| 7732-18-5 | Distilled water | 70.414% |

*The sodium alkyl paraben contains: sodium 4-(methoxycarbonyl) phenolate (CAS No. 5026-62-0; 0.199%), sodium 4-ethoxycarbonylphenoxide (CAS No. 35285-68-8; 0.047%) and sodium 4-propoxycarbonylphenoxide (CAS No. 35285-69-9; 0.030%).

The pH of the liquid was 6.2 and the density of the liquid was 1.08 g/mL. The liquid was green/blue in color.

3. Negative Control

The kit includes one bottle containing 2.8 mL of negative control solution having the chemical composition shown in Table 3.

TABLE 3

Chemical Composition of Negative Control Solution

| CAS Number | Chemical/Biological Substance Name | Wt/Wt % |
| --- | --- | --- |
| 7365-45-9 | HEPES | 1.260% |
| 910010-01-5 | 10% casein | 10.582% |
| 910010-06-2 | Base Matrix | 52.910% |
| 990001-12-8 | A56620 | 1.058% |
| 1186 | Sodium Alkyl Paraben (Nipasept)* | 0.317% |
| 3844-45-9 | Blue Dye | Trace |
| 910010-13-8 | Tartrazine | Trace |
| 7732-18-5 | Distilled Water | 33.871% |

*The sodium alkyl paraben contains: sodium 4-(methoxycarbonyl) phenolate (CAS No. 5026-62-0; 0.228%), sodium 4-ethoxycarbonylphenoxide (CAS No. 35285-68-8; 0.054%) and sodium 4-propoxycarbonylphenoxide (CAS No. 35285-69-9; 0.035%).

The pH of the solution was 7.6, and the density of the solution was 108 g/mL. The solution was blue in color.

4. Antibody Positive Control

The kit includes one bottle containing 1.8 mL of antibody positive control having the chemical composition shown in Table 4.

TABLE 4

Chemical Composition of Antibody Positive control

| CAS Number | Chemical/Biological Substance Name | Wt/Wt % |
| --- | --- | --- |
| 7365-45-9 | HEPES | 1.260% |
| 910010-01-5 | 10% Casein | 10.580% |
| 910010-06-2 | Base Matrix | 52.900% |
| 990001-12-8 | A56620 | 1.058% |
| 1186 | Sodium Alkyl Paraben (Nipasept)* | 0.317% |
| 910010-017 | Holly Red Dye | Trace |
| 910010-13-8 | Tartrazine | Trace |
| 990001-03-0 | HCV Positive Sera | 0.755% |
| 7732-18-5 | Distilled Water | 33.128% |

*The sodium alkyl paraben contains: sodium 4-(methoxycarbonyl) phenolate (CAS No. 5026-62-0; 0.228%), sodium 4-ethoxycarbonylphenoxide (CAS No. 35285-68-8; 0.054%) and sodium 4-propoxycarbonylphenoxide (CAS No. 35285-69-9; 0.035%).

The pH of the solution is 7.6 and the density of the solution is 1.08 g/mL. The solution was yellow in color.

5. Antigen Positive Control

The kit includes one bottle containing 1.8 ml of antigen positive control having the chemical composition of shown in Table 5.

TABLE 5

Chemical Composition of the Antigen Positive Control Solution

| CAS Number | Chemical/Biological Substance Name | Wt/Wt % |
| --- | --- | --- |
| 7647-14-5 | Sodium Chloride | 0.877% |
| 910010-01-5 | 10% Casein | 1.000% |
| 9005-64-5 | Tween 20 | 0.400% |
| 910010-017 | Holly Red Dye | 0.020% |
| 26628-22-8 | Sodium Azide | 0.008% |
| 1336-21-6 | Ammonium Hydroxide | 0.300% |
| 990001-12-6 | MBL 408 | Trace |
| 990001-12-7 | MBL 411 | Trace |
| 9048-46-8 | Bovine Serum Albumin 30% | Trace |
| 7732-18-5 | Distilled Water | 97.392% |

The pH of the solution was 10.8 to 11.21. The density of the solution was 1.00 g/mL, and solution was red in color.

6. Conjugate

The conjugate of the kit is provided in one bottle or three bottles containing 1.25 mL of freeze dried, horseradish peroxidase-labeled conjugate containing the antigenic recombinant NS 3 and core protein peptides together with the anti-core monoclonal antibodies. When reconstituted each bottle is sufficient for up to two plates.

7. Conjugate Diluent

The conjugate diluent of the kit is provided as one bottle or three bottles each containing 25 mL of diluent (sufficient to reconstitute one bottle of conjugate) having a chemical composition shown in Table 6.

TABLE 6

Chemical Composition of Conjugate Diluent

| CAS Number | Chemical/Biological Substance Name | Wt/Wt % |
| --- | --- | --- |
| 7365-45-9 | HEPES | 0.424% |
| 7647-14-5 | Sodium Chloride | 4.405% |
| 14933-09-6 | Zwittergent | 0.070% |
| 9002-93-1 | Triton X-100 | 0.142% |
| 9005-64-5 | Tween 20 | 0.072% |
| 8047-15-2 | Saponin | 2.122% |
| 151-21-3 | Sodium Dodecyl Sulphate (SDS) | 0.036% |
| 466 | Proclin 300 | 0.094% |
| 9048-46-8 | 30% BSA | 28.300% |
| 910010-13-4 | Succinylated Casein | 7.800% |
| 910010-01-5 | 10% Casein | 1.349% |
| 121-79-9 | N-Propyl Gallate | TRACE |
| 64-17-5 | Absolute Alcohol | 0.030% |
| 9003-99-0 | Horse Radish Peroxidase | 1.000% |
| 7732-18-5 | Distilled Water | 54.155% |

The pH of the solution was 6.8 and the density of the solution was 1.06 g/mL. The solution was yellow in color.

Reconstitution of Conjugate

Reconstitution of conjugate is done by tapping the bottle of conjugate gently on a solid surface to remove any material adhering to the stopper. The whole contents of the bottle of conjugate diluent is poured into the bottle of conjugate, the latter is recapped and mixed by gentle inversion. The conjugate is allowed to Dehydrate for at least 15 minutes with occasional swirling. The reconstituted conjugate is red in color.

After reconstitution the conjugate may be stored at 2-8° C. for up to 24 hours or frozen (−15° C. or colder) in aliquots for up to 5 months. The reconstituted conjugate can be freeze thawed up to three times.

8. Substrate Diluent

Substrate diluent is provided as one bottle containing 35 mL of a colorless solution. The substrate diluent contains 0.048% hydrogen peroxide solution, 4.233% tri-sodium citrate, and 95.719% distilled water. All percentages are calculated as weight/weight percentages. The pH of the diluent is 7.5 to 8.5, and the density of the diluent is 1.03 g/mL.

9. Substrate Concentrate

The substrate concentrate is provided in one bottle containing 35 mL, of substrate concentrate having a chemical composition shown in Table 7.

TABLE 7

Chemical Composition of the Substrate Concentrate

| CAS Number | Chemical/Biological Substance Name | Wt/Wt % |
|---|---|---|
| 64285-73-0 | 3,3',5,5'-tetramethylbenzidine dihydro-chloride | 0.038% |
| 5949-29-1 | Citric Acid (monohydrate) | 4.39% |
| 25100-12-3 | N-Cyclohexylhydroxylamine hydrochloride | 0.014% |
| 6381-92-6 | Ethylenediamine tetra acetic acid disodium salt dihydrate | 0.002% |
| 6132-04-3 | Tri-sodium Citrate | 0.01% |
| 62625-31-4 | m-Cresol purple sodium salt | 0.002% |
| 7732-18-5 | Water (distilled) | 95.544% |

The pH of the solution is 2.0±0.3, and the density of the solution is 1.02 g/mL. The solution is orange in color.

Substrate Solution

To prepare the Substrate Solution a volume of colorless Substrate Diluent is added to an equal volume of orange Substrate Concentrate, as indicated in Table 8 below, in a clean plastic vessel.

TABLE 8

Volume of Substrate Concentrate and Substrate Diluent required

| Number of Wells | | | | | | | | | | | Number of Plates | | | |
|---|---|---|---|---|---|---|---|---|---|---|---|---|---|---|
| 8 | 16 | 24 | 32 | 40 | 48 | 56 | 64 | 72 | 80 | 96 | 1 | 2 | 3 | 4 |
| Substrate Concentrate (ml) | | | | | | | | | | | | | | |
| 1 | 1.5 | 2 | 2.5 | 2.5 | 3 | 3.5 | 4 | 4.5 | 4.5 | 6 | 6 | 12 | 18 | 22 |
| Substrate Diluent (ml) | | | | | | | | | | | | | | |
| 1 | 1.5 | 2 | 2.5 | 2.5 | 3 | 3.5 | 4 | 4.5 | 4.5 | 6 | 6 | 12 | 18 | 22 |

Alternatively, the Substrate Solution may be made by pouring the entire contents of the bottle of Substrate Diluent into the bottle of Substrate Concentrate. On addition of the Substrate Diluent the Substrate Concentrate will change color from orange to yellow.

The prepared Substrate Solution is stable refrigerated (2 to 8° C.) or at 15 to 25° C. for up to two days but must be discarded if crystals have formed.

10. Wash Fluid

The kit includes one bottle or two bottles containing 125 mL of 20 times working strength Tween/Saline Wash Fluid. The 20 times working strength solution contains 1.714% Bronidox® (10% solution), 1.541% propane-1,2-diol, 0.173% 5-bromo-5-nitro-1,3-dioxane, 14.266% sodium chloride, 0.857% Tween 20, and 83.136% water. All percentages are weight/weight percentages. The pH of the solution is 7, and the density of the solution is 1.11 g/mL. The Wash Fluid is diluted one in twenty with either distilled or deionized water to give the required volume, or the entire contents of one bottle of Wash Fluid is diluted to a final volume of 2500 mL. When diluted, the Wash Fluid contains 0.01% Bronidox® preservative.

The working strength Wash Fluid is stored at 18 to 30° C. in a closed vessel under which conditions it will retain activity for one month.

Example 4

Sample Preparation and Storage

The following example describes the preparation and storage of samples to be tested using the immunoassay kit described in Example 3 Serum, EDTA plasma or citrate plasma samples may be used in the methods. Serum samples should be fully clotted, and any visible particulate matter removed from the sample by centrifugation. When the kit is used to assay samples from seroconversion panels, the samples may be used as provided by the supplier without any further treatment.

The samples are stored at 2 to 8° C. Samples not required for assay within 72 hours are removed from the clot or cell pellet and stored frozen (−15° C. or, colder). Multiple freeze-thaw cycles are avoided. This is particularly important as freeze thawing antigen-only samples as few as 5 times can reduce the signal by up to 25%. After thawing, ensure samples are thoroughly mixed before testing.

Example 5

Method for Semi-Automated Microplate Processors

The following describes an exemplary method that can be used with semi-automated microplate processors. The method can be carried out using the immunoassay kit described in Example 3. All reagents and samples and reagents are allowed to come to 18 to 30° C. before use. Immediately after use all reagents are returned to the recommended storage temperature. Any glassware to be used with the reagents is thoroughly washed with 2M hydrochloric acid and then rinsed with distilled water or high quality deionized water.

The method as described below allows for process control monitoring. Addition of the various components of the assay to the wells can be confirmed visually by examining the plate for the following colors. Sample Diluent is green in color. On addition of the sample or control the diluent will changes to blue. The color change will vary from sample to sample but some change should always be visible. Reconstituted Conjugate is red in color. Substrate Solution is initially yellow with any reactive wells becoming blue/green. On addition of Stop Solution the blue/green color of the reactives changes to orange while the non-reactive wells change to pink. The addition of sample or reagent can be confirmed using a microplate reader as follows: Sample diluent plus sample read at 570 or 620 nm with a reference at 690 nm, Conjugate reads at 490 nm with a reference at 690 nm, Substrate solution reads at 450 nm (no reference).

The method comprises the following steps:
1. Prepare the Wash Fluid, reconstitute the Conjugate.
2. Add 50 µl of Sample Diluent to each well.
3. Add 50 µl of Samples or 50 µl of Controls to the wells. The use of a white background will aid the visualization of sample addition.
4. Cover the wells with the lid and incubate for 60 minutes at 37° C.±1° C. (first incubation period).
5. At the end of the incubation period wash the plate as described under Wash Procedures. After washing is complete invert the plate and tap out any residual Wash Fluid onto absorbent paper.
6. Immediately add 120 µl of conjugate to each well.
7. Cover the wells with the lid and incubate for 60 minutes at 15-28° C. (second incubation period).
8. Prepare the substrate solution.
9. Repeat step 5.
10. Immediately after washing the plate, add 80 µl of substrate solution to each well.
11. Cover the wells with a lid and incubate for 30 minutes at 37° C.±1° C. (third incubation period). Keep away from direct sunlight.
12. Add 50 µl of stop solution. Suitable stop solutions comprise 0.5M to 2M sulfuric acid.
13. Within 15 minutes read the absorbance at 450 nm using 620 nm to 690 nm as the reference wavelength, if available. Blank the instrument on air (no plate in the carriage).

Wash Procedures

Protocols known in the art for recommended washers and procedures for verifying washers and analyzers can be used, or the following exemplary protocol can be used:

Protocol for Automated Stripwasher

Perform 5 wash cycles using working strength Wash Fluid. Ensure, where possible, that:
(i) Flow-through washing with a fill volume of 500 µl/well is used and/or that the well is completely filled.
(ii) The dispense height is set to completely fill the well with a slight positive meniscus, without causing an overflow.
(iii) The time taken to complete one aspirate/wash/soak cycle is approximately 30 seconds.
(iv) No liquid is left in the well (by use of a double aspirate step in the final cycle where possible).
(v) After washing is complete, invert the plate and tap out any residual Wash Fluid onto absorbent paper.
(vi) Do not allow the wells to become dry during the assay procedure

Example 6

Method for Fully Automated Microplate Processors

Using the immunoassay kit described in Example 3 and the general method described in Example 5, the incubation times for fully automated microplate processors should be adjusted as follows:

For the first and second incubations, incubation times between 60 and 70 minutes (65+/−5 minutes) may be programmed. For the third incubation, incubation times between 30 and 35 minutes (32.5+/−2.5 minutes) may be programmed.

Wells containing Sample Diluent may be left at 18 to 30° C. for up to 60 minutes before starting Step 4.

Example 7

Analysis of Results

Results of the immunoassay using the kit as described in Example 3 and the method of Example 5 or 6 can be analyzed as follows. Each plate must be considered separately when calculating and interpreting results of the assay. Approved software may be used for calculation and interpretation of results.

Negative Control
  Calculate the mean absorbance of the Negative Controls.
  If one of the Negative Control Wells has an absorbance greater than 0.25, discard that value and calculate the cut off based on the remaining Negative Control value.
  If both Negative Control values are greater than 0.25 the run is invalid.

Cut-Off Value
  Calculate the Cut-off value by adding 0.2 to the mean absorbance of the Negative Control For example:
Negative Control absorbance: Well 1=0.182
  Well 2=0.172
Mean Negative Control=(0.182+0.172)/2=0.177
Cut-off Value=0.177+0.2=0.37

Quality Control
  Results of an assay are valid if the following criteria for the controls are met:
Negative Control The Mean Absorbance is less than 0.25
Positive Controls The Absorbance is more than 0.8 above the mean absorbance of the Negative Control.
  Assays which do not meet these criteria should be repeated.

Interpretation of Results
  Samples giving an absorbance lower than the Cut-off value are considered non-reactive in the assay.
  Samples giving an absorbance greater than or equal to the Cut-off value are considered initially reactive in the assay. Unless local procedures state otherwise, such samples should be retested in duplicate using the original source. Samples that are reactive in at least one of the duplicate retests are reactive to HCV. Such samples should be further investigated and the results from this assay considered with any other clinical and/or supplementary testing information. Samples which are non-reactive in both wells on retest should be considered non-reactive in this assay.

Example 8

Determination of Diagnostic Sensitivity

A total of 509 specimens from patients with established hepatitis C infection were tested using the immunoassay kit described in Example 3 (using the semi-automated method described generally in Example 5).

All of the samples tested were found to be reactive. The diagnostic sensitivity of the method on this population of specimens was observed to the 100% (509/509) with an estimated lower 95% confidence limit of 99.28% by the binomial distribution.

The performance of the method was also tested for efficacy of detection in the early phase of HCV infection compared to antibody only assays by assessing performance on 30 commercially available seroconversion panels (Boston Biomedica, Bioclinical Partners and North American Biologicals) comprising 265 specimens in total. The results are shown in Table 9. In these studies the method detected 196 specimens as positive compared to 94 detected positive by an established assay for anti HCV antibody. In terms of time to first detection, this equates to detection in the method on average 20.57 days earlier than in the antibody only assay, with a range of 0 to 72 days earlier.

In this study, 10 of the 30 seroconversion panels included early specimens that were negative by both nucleic acid detection and serological assays. When comparing performance on these 10 panels the method detected infection on average 33.2 days earlier than the HCV antibody assay, and only 1.0 days later than nucleic acid testing (NAT) on average.

TABLE 9

Performance Assessment with 30 Seroconversion Panels

| Panel | Subtype | First day detected HCV RNA | Number of days delay versus HCV RNA positive bleed HCV Ab | Example 8 |
|---|---|---|---|---|
| BCP6211 | 1a | 140 | 42 | 0 |
| BCP6213 | 1a | 11 | 32 | 7 |
| BCP6222 | 1a | 17 | 23 | 0 |
| BCP6225 | 1a | 45 | 35 | 0 |
| BCP6227 | 1a | 42 | 32 | 0 |
| BCP9041 | 1a | 24 | 37 | 0 |
| PHV917 | 2b | 13 | 72 | 0 |
| BCP9054 | 3a | 56 | 3 | 0 |
| BCP9055 | NC | 31 | 34 | 3 |
| PHV901 | 1a | 65 | 32 | 0 |
| | | Mean: | 34.2 | 1.0 |

Example 9

Determination of Diagnostic Specificity #1

The immunoassay described in Example 3 and the methods described generally in Examples 5 and 6 are designed to meet the requirement of the Common Technical Specification (2002/364/EC) with specificity >99.5% in blood donor populations, and this requirement was exceeded in field trials at major blood donor centers. A total of 8292 specimens from routine donor specimens were screened at two blood donor centers using the immunoassay kit described in Example 3 (using the fully automated method described generally in Example 6).

In the study, 99.82% (8277/8292) of specimens were non-reactive with a lower 95% confidence limit of 99.70% by the binomial distribution. A total of 15/8292 presumed negative specimens were repeatedly reactive using the method (0.18%). Two other specimens in this study were identified as positive using the method according to the present invention, and PCR positive, but HCV antibody negative.

A total of 376 potentially cross-reactive specimens from patients with conditions unrelated to HCV infection were also tested. These included specimens from pregnant women, patients suffering with autoimmune disease and other acute viral infections. One of the specimens was found to be reactive with the method according to the present invention, giving a diagnostic specificity of 99.73% with a lower 95% confidence limit of 98.53% in this particular population. One specimen identified as positive using the combination assay and PCR, but negative on HCV antibody assay was excluded as true positive.

Example 10

Determination of Reproducibility

The reproducibility of the immunoassay kit described in Example 3 (using the fully automated method described generally in Example 6) was assessed by testing ten replicates of five panel members on four separate occasions. The results from the testing are summarized in Tables 10 and 11.

TABLE 10

Reproducibility - Reagent Lot 1

| Specimen | Number of Assays | Number of Replicates | Mean Absorbance | Intra-assay % CV | Inter-assay % CV |
|---|---|---|---|---|---|
| Ab Positive | 4 | 10 | 1.558 | 8.9 | 15.6 |
| QC1(Antigen) | 4 | 10 | 1.655 | 3.1 | 6.1 |
| QC2(Negative) | 4 | 10 | 0.118 | 4.8 | 5.0 |
| QC3(core) | 4 | 10 | 1.152 | 5.1 | 7.2 |
| QC4(NS3) | 4 | 10 | 0.874 | 4.0 | 8.1 |

TABLE 11

Reproducibility - Reagent Lot 2

| Specimen | Number of Assays | Number of Replicates | Mean Absorbance | Intra-assay % CV | Inter-assay % CV |
|---|---|---|---|---|---|
| Ab Positive | 4 | 10 | 1.731 | 7.8 | 10.1 |
| QC1(Antigen) | 4 | 10 | 1.114 | 4.1 | 10.2 |
| QC2(Negative) | 4 | 10 | 0.084 | 4.8 | 4.9 |
| QC3(core) | 4 | 10 | 1.398 | 4.2 | 6.0 |
| QC4(NS3) | 4 | 10 | 0.938 | 7.9 | 10.3 |

Example 11

Assessment of Sensitivity Against BBI Seroconversion Panel PHV907

The sensitivity of the immunoassay kit described in Example 3 (using the semi-automated method described generally in Example 5) was assessed in comparison to methods of detecting HCV by PCR (Roche AMPLICOR®) or by detecting anti-HCV antibodies (Murex HCV v3.0 antibody and Murex HCV v4.0 antibody) using a commercially available seroconversion panel (BBI PHV907, Boston Biomedica Inc). PCR and anti-HCV antibody data was taken from the supplier's panel data sheets. The results of the comparison are shown in Table 12 (values greater than 1.0 for the antibody (Ab) and combination assay are considered to be positive).

TABLE 12

Comparison of Combination Immunoassay with Antibody-Only Assays and NAT

| | Day | Roche PCR* | Murex V3 Ab | Murex V4 Ab | Combination Assay |
|---|---|---|---|---|---|
| PHV 907-1 | 0 | 3000000 | 0 | 0.11 | 1.638 |
| PHV 907-2 | 4 | 2000000 | 0 | 0.12 | 4.100 |
| PHV 907-3 | 7 | 1000000 | 0 | 0.12 | 3.297 |
| PHV 907-4 | 13 | 1000000 | 0.14 | 3.75 | 4.583 |
| PHV 907-5 | 18 | 1000000 | 1.58 | 4.19 | 6.5 |
| PHV 907-6 | 21 | 1000000 | 1.44 | 4.17 | 5.5 |
| PHV 907-7 | 164 | 1000000 | >5.0 | 4.11 | 8.3 |

*NAT data taken from panel manufacturer's data sheet.

The results indicated that the combination assay was able to detect HCV infection 13 days earlier than the Murex V3 and Murex V4 assays which detect anti-HCV antibodies only. The results also indicate that not all commercially available seroconversion panels have a PCR negative first bleed.

Example 12

Assessment of Sensitivity against Bioclinical Partners Seroconversion Panel 6222

The sensitivity of the immunoassay kit described in Example 3 (using the semi-automated method described generally in Example 5) against an alternate commercially available seroconversion panel (Bioclinical Partners, seroconversion panel 6222) was assessed in comparison to methods of detecting HCV by PCR or by detecting anti-HCV antibodies (Murex Anti HCV v3.0 (VK47/48) and Murex Anti HCV v4.0 (07F51). The results of this comparison are shown in Table 13 (values in this table that are greater than 1.0 for the antibody (Ab) and combination assay and greater than 0 for the PCR assay are considered to be positive).

TABLE 13

Comparison of Combination Immunoassay with Antibody-Only Assays and NAT

|  | Day | PCR* ($\times 10^6$/mL) | Murex V3 Ab | Murex V4 Ab | Combination Assay |
| --- | --- | --- | --- | --- | --- |
| 6222-1 | 0 | 0 | 0.007 | 0.007 | 0.476 |
| 6222-2 | 2 | 0 | 0.005 | 0.005 | 0.455 |
| 6222-3 | 17 | 0.29 | 0.01 | 0.01 | 1.693 |
| 6222-4 | 19 | 0.56 | 0.002 | 0.002 | 2.267 |
| 6222-5 | 24 | 0.71 | 0.026 | 0.026 | 3.979 |
| 6222-6 | 26 | 0.83 | 0.22 | 0.003 | 3.413 |
| 6222-7 | 36 | 1.6 | 0.79 | 0.043 | 5.923 |
| 6222-8 | 40 | 0.45 | 4.22 | 1.597 | 7.937 |

*NAT data taken from panel manufacturer's data sheet

The results indicated that the combination assay was able to detect HCV infection 23 days earlier than the assays used to detect anti-HCV antibodies.

Example 13

Assessment of Time of Detection Against Bioclinical Partners Seroconversion Panel 6211

The time of detection using the immunoassay kit described in Example 3 (using the semi-automated method described generally in Example 5) was assessed in comparison to time of detection using methods of detecting HCV by PCR, anti-HCV antibodies (Ortho 3) or HCV antigens (Ortho HCV antigen). Time of detection was measured against another commercially available seroconversion panel (Bioclinical Partners, seroconversion panel 6211). The results of this comparison are shown in Table 14 (values greater than 1.0 for the antibody (Ab), antigen and combination assays and greater than 0 for the PCR assay are considered to be positive).

TABLE 14

Comparison of Combination Immunoassay with Antibody-Only Assays and NAT

|  | Day | PCR* ($\times 10^6$/mL) | Ortho Antigen | Ortho 3 Antibody | Combination Assay |
| --- | --- | --- | --- | --- | --- |
| 6211-27 | 121 | 0 | 0.1 | 0.01 | 0.6 |
| 6211-28 | 140 | 3.9 | 5.1 | 0.01 | 3.1 |
| 6211-29 | 143 | 1.8 | 1.8 | 0.01 | 1.0 |
| 6211-30 | 147 | 2.3 | 5.2 | 0.01 | 1.4 |
| 6211-31 | 150 | >5 | 27.2 | 0.01 | 3.5 |
| 6211-32 | 154 | >5 | 53 | 0.01 | 8.2 |
| 6211-33 | 157 | >5 | 33 | 0.01 | 8.2 |
| 6211-34 | 161 | >5 | 48.5 | 0.01 | 8.2 |
| 6211-35 | 164 | >5 | 88 | 0.01 | 8.2 |
| 6211-36 | 168 | >5 | 91.6 | 0.01 | 8.2 |
| 6211-37 | 171 | >5 | 38.6 | 0.01 | 8.2 |
| 6211-38 | 182 | >5 | 52.9 | 0.85 | 8.2 |
| 6211-39 | 186 | >5 | 18.9 | 3.97 | 8.2 |
| 6211-40 | 189 | 5 | N/D | 4.15 | 8.2 |

*NAT data taken from panel manufacturer's data sheet

The results indicated that the combination assay was able to detect HCV infection 46 days earlier than assays used to detect anti-HCV antibodies in a sample. The results also indicate that the improvement in time of detection varies with the panel used to test the method.

Example 14

Assessment of Sensitivity Against BBI Seroconversion Panel PHV917

The sensitivity of the immunoassay kit described in Example 3 (using the semi-automated method described generally in Example 5) was assessed in comparison to sensitivity of methods of detecting HCV by PCR (Roche AMPLICOR®) or anti-HCV antibodies (Ortho). Sensitivity was measured against the commercially available BBI seroconversion panel PHV917.

The results of this comparison are shown in Table 15. O.D indicates optical density and S/CO indicates sample/cut-off values. In Table 14, values greater than 1.0 for the antibody (Ab) and combination assay (S/CO) are considered to be positive.

TABLE 15

Seroconversion Panel Showing Early Antigen Peak

|  | Day | Roche PCR‡ | Ortho 3 Antibody | Combination Assay (O.D.) | Combination Assay (S/CO) |
| --- | --- | --- | --- | --- | --- |
| PHV 917-1 | 0 | BLD* | 0 | 0.12 | 0.35 |
| PHV 917-2 | 13 | >5 × $10^5$ | 0 | 3.00 | 8.64 |
| PHV 917-3 | 20 | >5 × $10^5$ | 0 | 1.63 | 4.69 |
| PHV 917-4 | 22 | >5 × $10^5$ | 0 | 2.49 | 7.15 |
| PHV 917-5 | 85 | BQR¶ | >4.7 | 3.00 | 8.64 |
| PHV 917-6 | 131 | BQR¶ | >4.7 | 3.00 | 8.64 |
| PHV 917-7 | 135 | 3000 | >4.7 | 3.00 | 8.64 |
| PHV 917-8 | 138 | BLD* | >4.7 | 3.00 | 8.64 |
| PHV 917-9 | 146 | BLD* | >4.7 | 3.00 | 8.64 |

*BLD = below level of detection;
¶BQR = below quantifiable range;
‡NAT data taken from panel manufacturer's data sheet.

PHV917 is an example of a seroconversion panel which shows an early antigen peak and the results indicate that the combination assay gave a positive result 72 days earlier than the antibody only assay. NAT (Roche PCR assay) detected the same bleed positive as the combination assay, but went below the level of detection in the later bleeds, presumably as the patient clears circulating virus from the blood stream. These results thus also indicated that the HCV RNA and antigen peaks can be transient.

Example 15

Overall Sensitivity

As a representative example of the diagnostic sensitivity of the immunoassay kit described in Example 3 (using the semi-automated method described generally in Example 5), the kit was assessed against 34 commercially available seroconversion panels and these results compared to published data for Murex Anti HCV Version 4.0 (07F51), Ortho Anti HCV 3 (SAVe) antibody assays and nucleic acid testing (NAT) data (Roche AMPLICOR®).

The number of bleeds positive from the 34 seroconversion panels was assessed. The number of bleeds positive for NAT was 231. For the combination assay, the number of bleeds positive was 213 and for the antibody-only assay, number of bleeds positive was 103. Of the 34 seroconversion panels tested, therefore, the combination assay detected 84.86% of NAT positive samples (213/251). In addition, in 24 of the 34 panels (73.5% concordance), the combination assay was able to detect infection at the same bleed or time point as methods using nucleic acid testing (NAT). In contrast, methods using detection of anti-HCV antibodies only were able to detect the same positive bleed as methods using NAT in 3 of 34 panels (8.8% concordance).

In addition, the mean time to first detection using several commercially available assays ("Ortho 3", "Pasteur Plus", "ABBOTT PRISM®" and "AXSYM® 3.0") and the combination assay was compared to the theoretical best in class antibody assay, Day 0 is generated from the best available data from any on-market antibody only assay as measured against a single seroconversion panel. The combination assay is the most sensitive enzyme immunoassay (EIA) in 32/34 seroconversion panels tested. The combination assay gives an average gain of 12.7 days over the theoretical best in class antibody assay, and an average gain of 14.35 days over Ortho Anti-HCV 3 (SAVe). These results, together with results from additional experiments including those described herein, show that the combination assay closes the window of infection relative to antibody only assays by at least 2 weeks.

Example 16

Determination of Diagnostic Specificity #2

The diagnostic specificity of the immunoassay kit described in Example 3 (using the methods described generally in Examples 5 and 6), the "combination assay," was tested against a total of 3217 UK donor specimens. The results are shown in Table 16.

TABLE 16

Diagnostic Specificity using UK Blood Donor Specimens

| Assay | No. Tested | No. R.R.* | No. Negative | Specificity |
|---|---|---|---|---|
| Combination Assay | 3217 | 4 | 3213 | 99.88% |
| Murex HCV v4.0 Ab Assay | 3217 | 3 | 3214 | 99.91% |

*R.R = repeat reactive

Diagnostic specificity on 202 specimens of varying clinical conditions was observed to be 99.5%. All samples were concordantly positive on both the combination assay and Murex HCV v40 Ab.

Example 17

Early Detection of HCV Infection

The mean improvement in time of first detection for the immunoassay kit described in Example 3 (using the methods described generally in Examples 5 and 6), the "combination assay," was assessed by comparing results from screening 30/32 seroconversion panels (see Table 16) with the combination assay and Murex HCV v4.0 Ab Assay. 2/32 panels (6228 and SC-0402) were excluded as, while isolated early bleeds are antigen positive, these panels do not remain consistently positive in the combination assay after first detection and hence do not provide a true reflection of days gained.

The mean observed improvement in time of first detection for the combination assay compared to the HCV antibody assay was 20.57 days (see Table 17).

TABLE 17

Early Detection of HCV Infection using Combination Assay

| | | First day positive | | |
|---|---|---|---|---|
| | Panel | NAT | Combination Assay | Antibody-only Assay |
| 1 | PHV901 | 65 | 65 | 97 |
| 2 | PHV906 | 0 | 0 | 0 |
| 3 | PHV907 | 0 | 0 | 13 |
| 4 | PHV908 | 0 | 11 | 25 |
| 5 | PHV910 | 0 | 0 | 8 |
| 6 | PHV911 | 0 | 0 | 14 |
| 7 | PHV912 | 0 | 0 | 7 |
| 8 | PHV913 | 0 | 0 | 7 |
| 9 | PHV914 | 0 | 0 | 16 |
| 10 | PHV916 | 0 | 2 | 19 |
| 11 | PHV917 | 13 | 13 | 85 |
| 12 | 6215 | 0 | 0 | 20 |
| 13 | 6222 | 17 | 17 | 40 |
| 14 | 6211 | 140 | 140 | 182 |
| 15 | 6213 | 11 | 18 | 43 |
| 16 | 6214 | 0 | 0 | 32 |
| 17 | 6224 | 0 | 0 | 19 |
| 18 | 6225 | 45 | 45 | 80 |
| 19 | 6227 | 42 | 42 | 74 |
| 20 | 6229 | 0 | 0 | 20 |
| 21 | 9041 | 24 | 24 | 61 |
| 22 | 9054 | 56 | 56 | 59 |
| 23 | 9055 | 31 | 34 | 65 |
| 24 | 9944 | 0 | 0 | 25 |
| 25 | 9045 | 0 | 0 | 37 |
| 26 | SC0400 | 0 | 0 | 14 |
| 27 | SC0405 | 0 | 0 | 0 |
| 28 | SC0406 | 0 | 0 | 9 |
| 29 | SC0010 | 0 | 0 | 5 |
| 30 | SC0040 | 0 | 0 | 8 |
| | Total | 444 | 467 | 1084 |
| | Mean | 14.80 | 15.57 | 36.13 |
| | Days gain vs. HCV Ab | 21.33 | 20.57 | |

Example 18

Comparison to an Alternative Commercial HCV Ag/Ab Assay—Sensitivity

The performance of the immunoassay kit described in Example 3 (using the methods described generally in Examples 5 and 6), the "combination assay," was compared to that of the commercially available BioRad MonoLisa® HCV Ag-Ab Ultra kit. The BioRad kit was used following the manufacturer's instructions.

The following 28 seroconversion panels were used for comparison: PHV907, PHV901, PH1V915, PHV908, PHV905, PHV911, PHV909, PHV912, PHV910, PHV914, PHV913, NABI A, PHV916, SC-402, SC-400, SC-406, BCP6212, BCP6224, BCP6211, BCP6226, BCP6213, BCP6214, BCP6215, BCP6222, BCP6224, BCP6225, BCP6227 and BCP6228. In 25/28 panels tested the combination assay detected infection earlier than HCV Antibody only assay, and in 17/28 panels the combination assay detected infection earlier than the competitor Ag/Ab assay. The competitor Ag/Ab was ahead in 2/28 assays and equivalent in eight. In this study the combination assay reduced the mean time to detection by 14.4 days compared to HCV antibody assay and 4.6 days earlier than the competitor HCV Ag/Ab assay.

In 9 of the 28 panels the entire window period is represented, as in these panels the early samples are PCR negative. Performance on these panels is summarised in Table 18.

TABLE 18

Performance in Panels Representing Entire Window Period

| Panel | Subtype | First Day of Detection HCV RNA | No. Days Delay vs. First HCV RNA Positive Bleed | | |
|---|---|---|---|---|---|
| | | | Anti-HCV | BioRad Ag/Ab | Combination Assay |
| BCP6211 | 1a | 140 | 46 | 7 | 0 |
| BCP6213 | 1a | 11 | 32 | 25 | 7 |
| BCP6222 | 1a | 17 | 23 | 0 | 0 |
| BCP6225 | 1a | 45 | 35 | 2 | 0 |
| BCP6227 | 1a | 42 | 32 | 4 | 0 |
| BCP9041 | 1a | 24 | 38 | 0 | 0 |

TABLE 18-continued

Performance in Panels Representing Entire Window Period

| Panel | Subtype | First Day of Detection HCV RNA | No. Days Delay vs. First HCV RNA Positive Bleed | | |
|---|---|---|---|---|---|
| | | | Anti-HCV | BioRad Ag/Ab | Combination Assay |
| PHV917 | 2b | 13 | 73 | 0 | 0 |
| BCP9054 | 3a | 52 | 8 | 0 | 0 |
| BCP9055 | NC | 31 | 37 | 2 | 2 |
| | | Mean Delay: | 36.0 | 4.4 | 1.0 |

Example 19

Comparison to an Alternative Commercial HCV Ag/Ab Assay—Limit of Detection

The theoretical limit of limit of detection in terms of copies/mL nucleic acid the immunoassay kit described in Example 3 (using the methods described generally in Examples 5 and 6) was assessed by comparing S/CO ratios to viral load in a population of PCR positive/antibody negative samples from commercial seroconversion panels following the method described in Laperche et al., (*Transfusion*, 45:1965-1972 (2005)). 43/44 samples from the original paper were available for this study (see Table 19). The commercially available BioRad MonoLisa® HCV Ag-Ab Ultra kit was also assessed by this methodology. The BioRad kit was used following the manufacturer's instructions.

Figure 6:
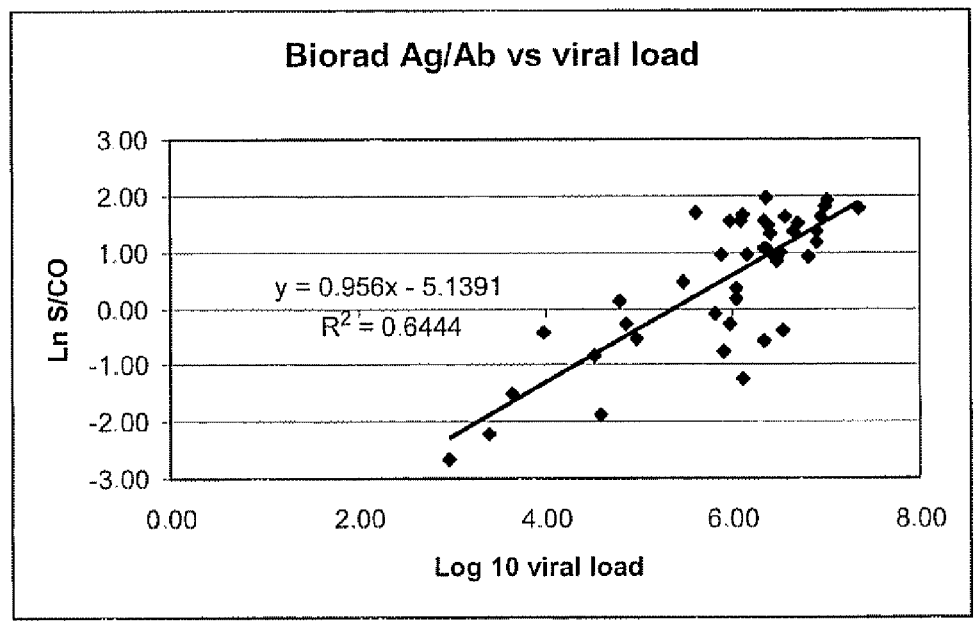
Figure 6:
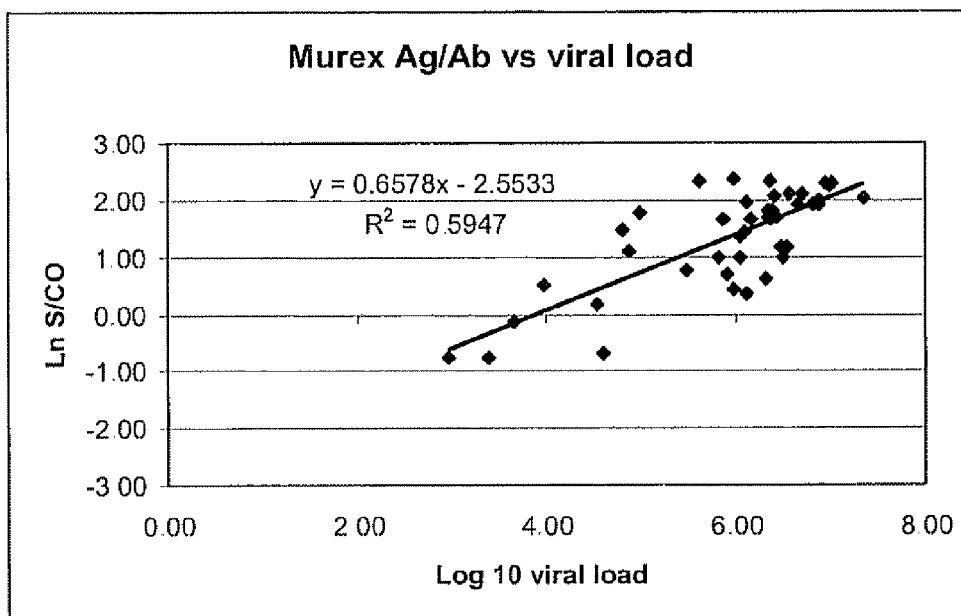

The results are shown in Table 19 and FIGS. 6A & B and are summarised in Table 20. Viral load endpoint was predicted by plotting $\log_{10}$ viral load vs. Ln S/CO and taking the intercept at Ln S/CO=0 (i.e the point at which S/CO=1). The results show that the combination assay in accordance with the present invention demonstrates earlier and more sensitive detection of HCV than the competitor Ag/Ab assay.

TABLE 19

Comparison to an Alternative Commercial HCV Ag/Ab Assay - Viral Load Endpoint

| | Panel | | Combination Assay | | | BioRad Ag/Ab | | | | Viral Load* |
|---|---|---|---|---|---|---|---|---|---|---|
| | | | S/CO | Log 10 | Ln | S/CO | Log 10 | Ln | NAT | Log 10 |
| 1 | 6211 | 28 | 3.287 | 0.517 | 1.19 | 0.67 | −0.174 | −0.40 | 3500000 | 6.54 |
| 2 | | 29 | 1.447 | 0.160 | 0.37 | 0.29 | −0.538 | −1.24 | 1300000 | 6.11 |
| 3 | | 30 | 1.867 | 0.271 | 0.62 | 0.57 | −0.244 | −0.56 | 2100000 | 6.32 |
| 4 | | 31 | 7.272 | 0.862 | 1.98 | 3.21 | 0.507 | 1.17 | 7700000 | 6.89 |
| 5 | | 32 | 9.568 | 0.981 | 2.26 | 6.17 | 0.790 | 1.82 | 9800000 | 6.99 |
| 6 | | 33 | 7.536 | 0.877 | 2.02 | 5.84 | 0.766 | 1.76 | 22000000 | 7.34 |
| 7 | | 34 | 9.896 | 0.995 | 2.29 | 6.85 | 0.836 | 1.92 | 10000000 | 7.00 |
| 8 | | 35 | 9.861 | 0.994 | 2.29 | 5.09 | 0.707 | 1.63 | 8600000 | 6.93 |
| 9 | | 36 | 8.322 | 0.920 | 2.12 | 4.58 | 0.661 | 1.52 | 4900000 | 6.69 |
| 10 | | 37 | 6.692 | 0.826 | 1.90 | 3.95 | 0.597 | 1.37 | 7700000 | 6.89 |
| 11 | 6213 | 4 | 0.472 | −0.326 | −0.75 | 0.11 | −0.959 | −2.21 | 2500 | 3.40 |
| 12 | | 5 | 0.879 | −0.056 | −0.13 | 0.22 | −0.658 | −1.51 | 4500 | 3.65 |
| 13 | | 6 | 1.163 | 0.066 | 0.15 | 0.44 | −0.357 | −0.82 | 34000 | 4.53 |
| 14 | | 7 | 5.845 | 0.767 | 1.77 | 0.58 | −0.237 | −0.54 | 95000 | 4.98 |
| 15 | | 8 | 2.972 | 0.473 | 1.09 | 0.75 | −0.125 | −0.29 | 74000 | 4.87 |
| 16 | | 9 | 2.689 | 0.430 | 0.99 | 0.9 | −0.046 | −0.11 | 660000 | 5.82 |
| 17 | | 10 | 5.262 | 0.721 | 1.66 | 2.56 | 0.408 | 0.94 | 750000 | 5.88 |
| 18 | 6222 | 3 | 3.849 | 0.585 | 1.35 | 1.19 | 0.076 | 0.17 | 1100000 | 6.04 |
| 19 | | 4 | 5.217 | 0.717 | 1.65 | 2.59 | 0.413 | 0.95 | 1400000 | 6.15 |
| 20 | | 5 | 10.753 | 1.032 | 2.38 | 4.61 | 0.664 | 1.53 | 940000 | 5.97 |
| 21 | | 6 | 4.245 | 0.628 | 1.45 | 4.68 | 0.670 | 1.54 | 1200000 | 6.08 |
| 22 | | 7 | 10.088 | 1.004 | 2.31 | 5.51 | 0.741 | 1.71 | 410000 | 5.61 |
| 23 | 6225 | 12 | 2.017 | 0.305 | 0.70 | 0.46 | −0.337 | −0.78 | 800000 | 5.90 |
| 24 | | 13 | 6.178 | 0.791 | 1.82 | 4.43 | 0.646 | 1.49 | 2400000 | 6.38 |
| 25 | | 14 | 5.382 | 0.731 | 1.68 | 4.68 | 0.670 | 1.54 | 2200000 | 6.34 |
| 26 | | 15 | 5.489 | 0.739 | 1.70 | 2.62 | 0.418 | 0.96 | 2700000 | 6.43 |

TABLE 19-continued

Comparison to an Alternative Commercial HCV Ag/Ab Assay - Viral Load Endpoint

| | | | Combination Assay | | | BioRad Ag/Ab | | | | Viral Load* |
|---|---|---|---|---|---|---|---|---|---|---|
| | Panel | | S/CO | Log 10 | Ln | S/CO | Log 10 | Ln | NAT | Log 10 |
| 27 | | 16 | 7.868 | 0.896 | 2.06 | 3.72 | 0.571 | 1.31 | 2500000 | 6.40 |
| 28 | | 17 | 1.530 | 0.185 | 0.43 | 0.75 | −0.125 | −0.29 | 940000 | 5.97 |
| 29 | 6227 | 4 | 1.627 | 0.211 | 0.49 | 0.64 | −0.194 | −0.45 | 9700 | 3.99 |
| 30 | | 5 | 4.389 | 0.642 | 1.48 | 1.13 | 0.053 | 0.12 | 64000 | 4.81 |
| 31 | 9041 | 2 | 2.140 | 0.330 | 0.76 | 1.58 | 0.199 | 0.46 | 300000 | 5.48 |
| 32 | | 3 | 7.046 | 0.848 | 1.95 | 5.32 | 0.726 | 1.67 | 1300000 | 6.11 |
| 33 | | 4 | 10.184 | 1.008 | 2.32 | 6.99 | 0.844 | 1.94 | 2300000 | 6.36 |
| 34 | 9054 | 7 | 0.460 | −0.337 | −0.78 | 0.07 | −1.155 | −2.66 | 930 | 2.97 |
| 35 | | 8 | 2.660 | 0.425 | 0.98 | 2.72 | 0.435 | 1.00 | 3200000 | 6.51 |
| 36 | 9055 | 6 | 0.495 | −0.305 | −0.70 | 0.15 | −0.824 | −1.90 | 40000 | 4.60 |
| 37 | | 7 | 6.899 | 0.839 | 1.93 | 3.87 | 0.588 | 1.35 | 4500000 | 6.65 |
| 38 | | 8 | 5.296 | 0.724 | 1.67 | 2.89 | 0.461 | 1.06 | 2300000 | 6.36 |
| 39 | | 9 | 2.639 | 0.421 | 0.97 | 1.45 | 0.161 | 0.37 | 1100000 | 6.04 |
| 40 | | 10 | 3.184 | 0.503 | 1.16 | 2.3 | 0.362 | 0.83 | 2900000 | 6.46 |
| 41 | PHV917 | 2 | 8.170 | 0.912 | 2.10 | 5.02 | 0.701 | 1.61 | 3600000 | 6.56 |
| 42 | | 3 | 6.130 | 0.787 | 1.81 | 2.88 | 0.459 | 1.06 | 2200000 | 6.34 |
| 43 | | 4 | 6.723 | 0.828 | 1.91 | 2.49 | 0.396 | 0.91 | 6300000 | 6.80 |

*Viral load data was taken from Laperche et al, Transfusion, 45: 1965-1972 (2005).

TABLE 20

Comparison to an Alternative Commercial HCV Ag/Ab Assay - Summary

| Parameter | BioRad Ag/Ab (published data) | Combination Assay |
|---|---|---|
| No. of Pre-seroconversion NAT Positive Samples Detected | 29/43 (67.4%) | 39/43 (90.7%) |
| Predicted Viral Endpoint ($\log_{10}$ IU/mL) | 5.38 (5.25) | 3.88 |
| Range of Viral Load (mean) | | |
| HCV Ag/Ab negative samples | 930 – 3.5 × $10^6$ (7 × $10^5$) | 930 – 4 × $10^4$ (1.1 × $10^4$) |
| HCV Ag/Ab positive samples | 6.4 × $10^4$ – 2.2 × $10^7$ (4 × $10^6$) | 9700 – 2.2 × $10^7$ (1.4 × $10^6$) |

Although the invention has been described with reference to certain specific embodiments, various modifications thereof will be apparent to those skilled in the art without departing from the spirit and scope of the invention as outlined in the claims appended hereto.

The disclosure of all patents, publications, including published patent applications, and database entries referenced in this specification are specifically incorporated by reference in their entirety to the same extent as if each such individual patent, publication, and database entry were specifically and individually indicated to be incorporated by reference.

SEQUENCE LISTING

```
<160> NUMBER OF SEQ ID NOS: 98

<210> SEQ ID NO 1
<211> LENGTH: 189
<212> TYPE: PRT
<213> ORGANISM: Hepatitis C Virus

<400> SEQUENCE: 1

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Thr Trp Ala Pro Gly Tyr
65                  70                  75                  80

Pro Trp Pro Leu Tyr Gly Asn Glu Gly Cys Gly Trp Ala Gly Trp Leu
```

```
                 85                  90                  95

Leu Ser Pro Arg Gly Ser Arg Pro Ser Trp Gly Pro Thr Asp Pro Arg
            100                 105                 110

Arg Arg Ser Arg Asn Leu Gly Lys Val Ile Asp Thr Thr Cys Gly Phe
            115                 120                 125

Ala Asp Leu Met Gly Tyr Ile Pro Leu Val Gly Ala Pro Leu Gly Gly
    130                 135                 140

Ala Ala Arg Ala Leu Ala His Gly Val Arg Val Leu Glu Asp Gly Val
145                 150                 155                 160

Asn Tyr Ala Thr Gly Asn Leu Gly Cys Ser Phe Ser Ile Phe Leu Leu
                165                 170                 175

Ala Leu Leu Ser Cys Leu Thr Ile Pro Ala Ser Ala Tyr
            180                 185

<210> SEQ ID NO 2
<211> LENGTH: 191
<212> TYPE: PRT
<213> ORGANISM: Hepatitis C Virus

<400> SEQUENCE: 2

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
        130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala
            180                 185                 190

<210> SEQ ID NO 3
<211> LENGTH: 15
<212> TYPE: PRT
<213> ORGANISM: Hepatitis C Virus

<400> SEQUENCE: 3

Asn Arg Arg Pro Gln Asp Val Lys Phe Pro Gly Gly Gly Gln Ile
1               5                   10                  15

<210> SEQ ID NO 4
<211> LENGTH: 12
<212> TYPE: PRT
```

```
<213> ORGANISM: Hepatitis C Virus

<400> SEQUENCE: 4

Gly Val Tyr Leu Leu Pro Arg Arg Gly Pro Arg Leu
1               5                   10

<210> SEQ ID NO 5
<211> LENGTH: 20
<212> TYPE: PRT
<213> ORGANISM: Hepatitis C Virus

<400> SEQUENCE: 5

Thr Arg Lys Thr Ser Glu Arg Ser Gln Pro Arg Gly Arg Arg Gln Pro
1               5                   10                  15

Ile Pro Lys Ala
            20

<210> SEQ ID NO 6
<211> LENGTH: 4
<212> TYPE: PRT
<213> ORGANISM: Hepatitis C Virus

<400> SEQUENCE: 6

Gln Ile Val Gly
1

<210> SEQ ID NO 7
<211> LENGTH: 12
<212> TYPE: PRT
<213> ORGANISM: Hepatitis C Virus

<400> SEQUENCE: 7

Met Ser Thr Asn Pro Lys Pro Gln Arg Lys Thr Lys
1               5                   10

<210> SEQ ID NO 8
<211> LENGTH: 12
<212> TYPE: PRT
<213> ORGANISM: Hepatitis C Virus

<400> SEQUENCE: 8

Pro Lys Pro Gln Arg Lys Thr Lys Arg Asn Thr Asn
1               5                   10

<210> SEQ ID NO 9
<211> LENGTH: 12
<212> TYPE: PRT
<213> ORGANISM: Hepatitis C Virus

<400> SEQUENCE: 9

Arg Lys Thr Lys Arg Asn Thr Asn Arg Arg Pro Gln
1               5                   10

<210> SEQ ID NO 10
<211> LENGTH: 12
<212> TYPE: PRT
<213> ORGANISM: Hepatitis C Virus

<400> SEQUENCE: 10

Arg Asn Thr Asn Arg Arg Pro Gln Asp Val Lys Phe
1               5                   10

<210> SEQ ID NO 11
<211> LENGTH: 12
```

```
<212> TYPE: PRT
<213> ORGANISM: Hepatitis C Virus

<400> SEQUENCE: 11

Arg Arg Pro Gln Asp Val Lys Phe Pro Gly Gly Gly
 1               5                  10

<210> SEQ ID NO 12
<211> LENGTH: 12
<212> TYPE: PRT
<213> ORGANISM: Hepatitis C Virus

<400> SEQUENCE: 12

Asp Val Lys Phe Pro Gly Gly Gly Gln Ile Val Gly
 1               5                  10

<210> SEQ ID NO 13
<211> LENGTH: 12
<212> TYPE: PRT
<213> ORGANISM: Hepatitis C Virus

<400> SEQUENCE: 13

Pro Gly Gly Gly Gln Ile Val Gly Gly Val Tyr Leu
 1               5                  10

<210> SEQ ID NO 14
<211> LENGTH: 12
<212> TYPE: PRT
<213> ORGANISM: Hepatitis C Virus

<400> SEQUENCE: 14

Gln Ile Val Gly Gly Val Tyr Leu Leu Pro Arg Arg
 1               5                  10

<210> SEQ ID NO 15
<211> LENGTH: 12
<212> TYPE: PRT
<213> ORGANISM: Hepatitis C Virus

<400> SEQUENCE: 15

Gly Val Tyr Leu Leu Pro Arg Arg Gly Pro Arg Leu
 1               5                  10

<210> SEQ ID NO 16
<211> LENGTH: 12
<212> TYPE: PRT
<213> ORGANISM: Hepatitis C Virus

<400> SEQUENCE: 16

Leu Pro Arg Arg Gly Pro Arg Leu Gly Val Arg Ala
 1               5                  10

<210> SEQ ID NO 17
<211> LENGTH: 12
<212> TYPE: PRT
<213> ORGANISM: Hepatitis C Virus

<400> SEQUENCE: 17

Gly Pro Arg Leu Gly Val Arg Ala Thr Arg Lys Thr
 1               5                  10

<210> SEQ ID NO 18
<211> LENGTH: 12
<212> TYPE: PRT
<213> ORGANISM: Hepatitis C Virus
```

```
<400> SEQUENCE: 18

Gly Val Arg Ala Thr Arg Lys Thr Ser Glu Arg Ser
1               5                   10

<210> SEQ ID NO 19
<211> LENGTH: 12
<212> TYPE: PRT
<213> ORGANISM: Hepatitis C Virus

<400> SEQUENCE: 19

Thr Arg Lys Thr Ser Glu Arg Ser Gln Pro Arg Gly
1               5                   10

<210> SEQ ID NO 20
<211> LENGTH: 12
<212> TYPE: PRT
<213> ORGANISM: Hepatitis C Virus

<400> SEQUENCE: 20

Ser Glu Arg Ser Gln Pro Arg Gly Arg Arg Gln Pro
1               5                   10

<210> SEQ ID NO 21
<211> LENGTH: 12
<212> TYPE: PRT
<213> ORGANISM: Hepatitis C Virus

<400> SEQUENCE: 21

Gln Pro Arg Gly Arg Arg Gln Pro Ile Pro Lys Ala
1               5                   10

<210> SEQ ID NO 22
<211> LENGTH: 12
<212> TYPE: PRT
<213> ORGANISM: Hepatitis C Virus

<400> SEQUENCE: 22

Arg Arg Gln Pro Ile Pro Lys Ala Arg Arg Pro Glu
1               5                   10

<210> SEQ ID NO 23
<211> LENGTH: 12
<212> TYPE: PRT
<213> ORGANISM: Hepatitis C Virus

<400> SEQUENCE: 23

Ile Pro Lys Ala Arg Arg Pro Glu Gly Arg Thr Trp
1               5                   10

<210> SEQ ID NO 24
<211> LENGTH: 11
<212> TYPE: PRT
<213> ORGANISM: Hepatitis C Virus

<400> SEQUENCE: 24

Arg Arg Pro Glu Gly Arg Thr Trp Ala Pro Gly
1               5                   10

<210> SEQ ID NO 25
<211> LENGTH: 11
<212> TYPE: PRT
<213> ORGANISM: Hepatitis C Virus

<400> SEQUENCE: 25
```

```
Gly Arg Thr Trp Ala Pro Gly Tyr Pro Trp Pro
1               5                   10

<210> SEQ ID NO 26
<211> LENGTH: 11
<212> TYPE: PRT
<213> ORGANISM: Hepatitis C Virus

<400> SEQUENCE: 26

Ala Pro Gly Tyr Pro Trp Pro Leu Tyr Gly Asn
1               5                   10

<210> SEQ ID NO 27
<211> LENGTH: 12
<212> TYPE: PRT
<213> ORGANISM: Hepatitis C Virus

<400> SEQUENCE: 27

Tyr Pro Trp Pro Leu Tyr Gly Asn Glu Gly Cys Gly
1               5                   10

<210> SEQ ID NO 28
<211> LENGTH: 12
<212> TYPE: PRT
<213> ORGANISM: Hepatitis C Virus

<400> SEQUENCE: 28

Leu Tyr Gly Asn Glu Gly Cys Gly Trp Ala Gly Trp
1               5                   10

<210> SEQ ID NO 29
<211> LENGTH: 12
<212> TYPE: PRT
<213> ORGANISM: Hepatitis C Virus

<400> SEQUENCE: 29

Glu Gly Cys Gly Trp Ala Gly Trp Leu Leu Ser Pro
1               5                   10

<210> SEQ ID NO 30
<211> LENGTH: 12
<212> TYPE: PRT
<213> ORGANISM: Hepatitis C Virus

<400> SEQUENCE: 30

Trp Ala Gly Trp Leu Leu Ser Pro Arg Gly Ser Arg
1               5                   10

<210> SEQ ID NO 31
<211> LENGTH: 12
<212> TYPE: PRT
<213> ORGANISM: Hepatitis C Virus

<400> SEQUENCE: 31

Leu Leu Ser Pro Arg Gly Ser Arg Pro Ser Trp Gly
1               5                   10

<210> SEQ ID NO 32
<211> LENGTH: 13
<212> TYPE: PRT
<213> ORGANISM: Hepatitis C Virus

<400> SEQUENCE: 32

Arg Gly Ser Ser Arg Pro Ser Trp Gly Pro Thr Asp Pro
```

```
1               5                   10
```

<210> SEQ ID NO 33
<211> LENGTH: 12
<212> TYPE: PRT
<213> ORGANISM: Hepatitis C Virus

<400> SEQUENCE: 33

```
Pro Ser Trp Gly Pro Thr Asp Pro Arg Arg Ser
1               5                   10
```

<210> SEQ ID NO 34
<211> LENGTH: 12
<212> TYPE: PRT
<213> ORGANISM: Hepatitis C Virus

<400> SEQUENCE: 34

```
Pro Thr Asp Pro Arg Arg Arg Ser Arg Asn Leu Gly
1               5                   10
```

<210> SEQ ID NO 35
<211> LENGTH: 12
<212> TYPE: PRT
<213> ORGANISM: Hepatitis C Virus

<400> SEQUENCE: 35

```
Arg Arg Arg Ser Arg Asn Leu Gly Lys Val Ile Asp
1               5                   10
```

<210> SEQ ID NO 36
<211> LENGTH: 11
<212> TYPE: PRT
<213> ORGANISM: Hepatitis C Virus

<400> SEQUENCE: 36

```
Arg Asn Leu Gly Lys Val Ile Asp Thr Thr Cys
1               5                   10
```

<210> SEQ ID NO 37
<211> LENGTH: 11
<212> TYPE: PRT
<213> ORGANISM: Hepatitis C Virus

<400> SEQUENCE: 37

```
Lys Val Ile Asp Thr Thr Cys Gly Phe Ala Asp
1               5                   10
```

<210> SEQ ID NO 38
<211> LENGTH: 11
<212> TYPE: PRT
<213> ORGANISM: Hepatitis C Virus

<400> SEQUENCE: 38

```
Thr Thr Cys Gly Phe Ala Asp Leu Met Gly Tyr
1               5                   10
```

<210> SEQ ID NO 39
<211> LENGTH: 12
<212> TYPE: PRT
<213> ORGANISM: Hepatitis C Virus

<400> SEQUENCE: 39

```
Gly Phe Ala Asp Leu Met Gly Tyr Ile Pro Leu Val
1               5                   10
```

```
<210> SEQ ID NO 40
<211> LENGTH: 12
<212> TYPE: PRT
<213> ORGANISM: Hepatitis C Virus

<400> SEQUENCE: 40

Leu Met Gly Tyr Ile Pro Leu Val Gly Ala Pro Leu
1               5                   10

<210> SEQ ID NO 41
<211> LENGTH: 11
<212> TYPE: PRT
<213> ORGANISM: Hepatitis C Virus

<400> SEQUENCE: 41

Ile Pro Leu Val Gly Ala Pro Leu Gly Gly Ala
1               5                   10

<210> SEQ ID NO 42
<211> LENGTH: 12
<212> TYPE: PRT
<213> ORGANISM: Hepatitis C Virus

<400> SEQUENCE: 42

Gly Ala Pro Leu Gly Gly Ala Ala Arg Ala Leu Ala
1               5                   10

<210> SEQ ID NO 43
<211> LENGTH: 12
<212> TYPE: PRT
<213> ORGANISM: Hepatitis C Virus

<400> SEQUENCE: 43

Gly Gly Ala Ala Arg Ala Leu Ala His Gly Val Arg
1               5                   10

<210> SEQ ID NO 44
<211> LENGTH: 12
<212> TYPE: PRT
<213> ORGANISM: Hepatitis C Virus

<400> SEQUENCE: 44

Arg Ala Leu Ala His Gly Val Arg Val Leu Glu Asp
1               5                   10

<210> SEQ ID NO 45
<211> LENGTH: 12
<212> TYPE: PRT
<213> ORGANISM: Hepatitis C Virus

<400> SEQUENCE: 45

His Gly Val Arg Val Leu Glu Asp Gly Val Asn Tyr
1               5                   10

<210> SEQ ID NO 46
<211> LENGTH: 12
<212> TYPE: PRT
<213> ORGANISM: Hepatitis C Virus

<400> SEQUENCE: 46

Val Leu Glu Asp Gly Val Asn Tyr Ala Thr Gly Asn
1               5                   10

<210> SEQ ID NO 47
```

<211> LENGTH: 11
<212> TYPE: PRT
<213> ORGANISM: Hepatitis C Virus

<400> SEQUENCE: 47

Gly Val Asn Tyr Ala Thr Gly Asn Leu Gly Cys
1 5 10

<210> SEQ ID NO 48
<211> LENGTH: 11
<212> TYPE: PRT
<213> ORGANISM: Hepatitis C Virus

<400> SEQUENCE: 48

Ala Thr Gly Asn Leu Gly Cys Ser Phe Ser Ile
1 5 10

<210> SEQ ID NO 49
<211> LENGTH: 11
<212> TYPE: PRT
<213> ORGANISM: Hepatitis C Virus

<400> SEQUENCE: 49

Leu Gly Cys Ser Phe Ser Ile Phe Leu Leu Ala
1 5 10

<210> SEQ ID NO 50
<211> LENGTH: 12
<212> TYPE: PRT
<213> ORGANISM: Hepatitis C Virus

<400> SEQUENCE: 50

Ser Phe Ser Ile Phe Leu Leu Ala Leu Leu Ser Cys
1 5 10

<210> SEQ ID NO 51
<211> LENGTH: 12
<212> TYPE: PRT
<213> ORGANISM: Hepatitis C Virus

<400> SEQUENCE: 51

Phe Leu Leu Ala Leu Leu Ser Cys Leu Thr Ile Pro
1 5 10

<210> SEQ ID NO 52
<211> LENGTH: 12
<212> TYPE: PRT
<213> ORGANISM: Hepatitis C Virus

<400> SEQUENCE: 52

Leu Leu Ser Cys Leu Thr Ile Pro Ala Ser Ala Tyr
1 5 10

<210> SEQ ID NO 53
<211> LENGTH: 12
<212> TYPE: PRT
<213> ORGANISM: Hepatitis C Virus

<400> SEQUENCE: 53

Arg Arg Ser Thr Gly Lys Ser Trp Gly Lys Pro Gly
1 5 10

<210> SEQ ID NO 54
<211> LENGTH: 16
<212> TYPE: PRT

<213> ORGANISM: Hepatitis C Virus

<400> SEQUENCE: 54

Asn Arg Arg Pro Gln Asp Val Lys Phe Pro Gly Gly Gly Gln Ile Cys
1 5 10 15

<210> SEQ ID NO 55
<211> LENGTH: 12
<212> TYPE: PRT
<213> ORGANISM: Hepatitis C Virus
<220> FEATURE:
<223> OTHER INFORMATION: SAMSA functional group at Gly-1

<400> SEQUENCE: 55

Gly Val Tyr Leu Leu Pro Arg Arg Gly Pro Arg Leu
1 5 10

<210> SEQ ID NO 56
<211> LENGTH: 20
<212> TYPE: PRT
<213> ORGANISM: Hepatitis C Virus
<220> FEATURE:
<223> OTHER INFORMATION: SAMSA functional group and 3 aminohexanoic acid (Ahx) spacers at Thr-1

<400> SEQUENCE: 56

Thr Arg Lys Thr Ser Glu Arg Ser Gln Pro Arg Gly Arg Arg Gln Pro
1 5 10 15

Ile Pro Lys Ala
20

<210> SEQ ID NO 57
<211> LENGTH: 15
<212> TYPE: PRT
<213> ORGANISM: Hepatitis C Virus
<220> FEATURE:
<223> OTHER INFORMATION: SAMSA functional group and aminohexanoic acid (Ahx) spacer at Asn-1

<400> SEQUENCE: 57

Asn Arg Arg Pro Gln Asp Val Lys Phe Pro Gly Gly Gly Gln Ile
1 5 10 15

<210> SEQ ID NO 58
<211> LENGTH: 12
<212> TYPE: PRT
<213> ORGANISM: Hepatitis C Virus
<220> FEATURE:
<223> OTHER INFORMATION: SAMSA functional group and 3 aminohexanoic acid (Ahx) spacers at Gly-1

<400> SEQUENCE: 58

Gly Val Tyr Leu Leu Pro Arg Arg Gly Pro Arg Leu
1 5 10

<210> SEQ ID NO 59
<211> LENGTH: 20
<212> TYPE: PRT
<213> ORGANISM: Hepatitis C Virus
<220> FEATURE:
<223> OTHER INFORMATION: SAMSA functional group and aminohexanoic acid (Ahx) spacer at Thr-1

<400> SEQUENCE: 59

Thr Arg Lys Thr Ser Glu Arg Ser Gln Pro Arg Gly Arg Arg Gln Pro
1 5 10 15

Ile Pro Lys Ala
                20

<210> SEQ ID NO 60
<211> LENGTH: 4
<212> TYPE: PRT
<213> ORGANISM: Hepatitis C Virus

<400> SEQUENCE: 60

Asn Arg Arg Pro
1

<210> SEQ ID NO 61
<211> LENGTH: 4
<212> TYPE: PRT
<213> ORGANISM: Hepatitis C Virus

<400> SEQUENCE: 61

Arg Arg Pro Gln
1

<210> SEQ ID NO 62
<211> LENGTH: 4
<212> TYPE: PRT
<213> ORGANISM: Hepatitis C Virus

<400> SEQUENCE: 62

Arg Pro Gln Asp
1

<210> SEQ ID NO 63
<211> LENGTH: 4
<212> TYPE: PRT
<213> ORGANISM: Hepatitis C Virus

<400> SEQUENCE: 63

Pro Gln Asp Val
1

<210> SEQ ID NO 64
<211> LENGTH: 4
<212> TYPE: PRT
<213> ORGANISM: Hepatitis C Virus

<400> SEQUENCE: 64

Gln Asp Val Lys
1

<210> SEQ ID NO 65
<211> LENGTH: 4
<212> TYPE: PRT
<213> ORGANISM: Hepatitis C Virus

<400> SEQUENCE: 65

Asp Val Lys Phe
1

<210> SEQ ID NO 66
<211> LENGTH: 4
<212> TYPE: PRT
<213> ORGANISM: Hepatitis C Virus

<400> SEQUENCE: 66

Val Lys Phe Pro
1

```
<210> SEQ ID NO 67
<211> LENGTH: 4
<212> TYPE: PRT
<213> ORGANISM: Hepatitis C Virus

<400> SEQUENCE: 67

Lys Phe Pro Gly
 1

<210> SEQ ID NO 68
<211> LENGTH: 4
<212> TYPE: PRT
<213> ORGANISM: Hepatitis C Virus

<400> SEQUENCE: 68

Phe Pro Gly Gly
 1

<210> SEQ ID NO 69
<211> LENGTH: 4
<212> TYPE: PRT
<213> ORGANISM: Hepatitis C Virus

<400> SEQUENCE: 69

Pro Gly Gly Gly
 1

<210> SEQ ID NO 70
<211> LENGTH: 4
<212> TYPE: PRT
<213> ORGANISM: Hepatitis C Virus

<400> SEQUENCE: 70

Gly Gly Gly Gln
 1

<210> SEQ ID NO 71
<211> LENGTH: 4
<212> TYPE: PRT
<213> ORGANISM: Hepatitis C Virus

<400> SEQUENCE: 71

Gly Gly Gln Ile
 1

<210> SEQ ID NO 72
<211> LENGTH: 4
<212> TYPE: PRT
<213> ORGANISM: Hepatitis C Virus

<400> SEQUENCE: 72

Gly Val Tyr Leu
 1

<210> SEQ ID NO 73
<211> LENGTH: 4
<212> TYPE: PRT
<213> ORGANISM: Hepatitis C Virus

<400> SEQUENCE: 73

Val Tyr Leu Leu
 1
```

```
<210> SEQ ID NO 74
<211> LENGTH: 4
<212> TYPE: PRT
<213> ORGANISM: Hepatitis C Virus

<400> SEQUENCE: 74

Tyr Leu Leu Pro
 1

<210> SEQ ID NO 75
<211> LENGTH: 4
<212> TYPE: PRT
<213> ORGANISM: Hepatitis C Virus

<400> SEQUENCE: 75

Leu Leu Pro Arg
 1

<210> SEQ ID NO 76
<211> LENGTH: 4
<212> TYPE: PRT
<213> ORGANISM: Hepatitis C Virus

<400> SEQUENCE: 76

Leu Pro Arg Arg
 1

<210> SEQ ID NO 77
<211> LENGTH: 4
<212> TYPE: PRT
<213> ORGANISM: Hepatitis C Virus

<400> SEQUENCE: 77

Pro Arg Arg Gly
 1

<210> SEQ ID NO 78
<211> LENGTH: 4
<212> TYPE: PRT
<213> ORGANISM: Hepatitis C Virus

<400> SEQUENCE: 78

Arg Arg Gly Pro
 1

<210> SEQ ID NO 79
<211> LENGTH: 4
<212> TYPE: PRT
<213> ORGANISM: Hepatitis C Virus

<400> SEQUENCE: 79

Arg Gly Pro Arg
 1

<210> SEQ ID NO 80
<211> LENGTH: 4
<212> TYPE: PRT
<213> ORGANISM: Hepatitis C Virus

<400> SEQUENCE: 80

Gly Pro Arg Leu
 1

<210> SEQ ID NO 81
<211> LENGTH: 4
```

```
<212> TYPE: PRT
<213> ORGANISM: Hepatitis C Virus

<400> SEQUENCE: 81

Thr Arg Lys Thr
1

<210> SEQ ID NO 82
<211> LENGTH: 4
<212> TYPE: PRT
<213> ORGANISM: Hepatitis C Virus

<400> SEQUENCE: 82

Arg Lys Thr Ser
1

<210> SEQ ID NO 83
<211> LENGTH: 4
<212> TYPE: PRT
<213> ORGANISM: Hepatitis C Virus

<400> SEQUENCE: 83

Lys Thr Ser Glu
1

<210> SEQ ID NO 84
<211> LENGTH: 4
<212> TYPE: PRT
<213> ORGANISM: Hepatitis C Virus

<400> SEQUENCE: 84

Thr Ser Glu Arg
1

<210> SEQ ID NO 85
<211> LENGTH: 4
<212> TYPE: PRT
<213> ORGANISM: Hepatitis C Virus

<400> SEQUENCE: 85

Ser Glu Arg Ser
1

<210> SEQ ID NO 86
<211> LENGTH: 4
<212> TYPE: PRT
<213> ORGANISM: Hepatitis C Virus

<400> SEQUENCE: 86

Glu Arg Ser Gln
1

<210> SEQ ID NO 87
<211> LENGTH: 4
<212> TYPE: PRT
<213> ORGANISM: Hepatitis C Virus

<400> SEQUENCE: 87

Arg Ser Gln Pro
1

<210> SEQ ID NO 88
<211> LENGTH: 4
<212> TYPE: PRT
<213> ORGANISM: Hepatitis C Virus
```

<400> SEQUENCE: 88

Ser Gln Pro Arg
1

<210> SEQ ID NO 89
<211> LENGTH: 4
<212> TYPE: PRT
<213> ORGANISM: Hepatitis C Virus

<400> SEQUENCE: 89

Gln Pro Arg Gly
1

<210> SEQ ID NO 90
<211> LENGTH: 4
<212> TYPE: PRT
<213> ORGANISM: Hepatitis C Virus

<400> SEQUENCE: 90

Pro Arg Gly Arg
1

<210> SEQ ID NO 91
<211> LENGTH: 4
<212> TYPE: PRT
<213> ORGANISM: Hepatitis C Virus

<400> SEQUENCE: 91

Arg Gly Arg Arg
1

<210> SEQ ID NO 92
<211> LENGTH: 4
<212> TYPE: PRT
<213> ORGANISM: Hepatitis C Virus

<400> SEQUENCE: 92

Gly Arg Arg Gln
1

<210> SEQ ID NO 93
<211> LENGTH: 4
<212> TYPE: PRT
<213> ORGANISM: Hepatitis C Virus

<400> SEQUENCE: 93

Arg Arg Gln Pro
1

<210> SEQ ID NO 94
<211> LENGTH: 4
<212> TYPE: PRT
<213> ORGANISM: Hepatitis C Virus

<400> SEQUENCE: 94

Arg Gln Pro Ile
1

<210> SEQ ID NO 95
<211> LENGTH: 4
<212> TYPE: PRT
<213> ORGANISM: Hepatitis C Virus

<400> SEQUENCE: 95

```
<210> SEQ ID NO 96
<211> LENGTH: 4
<212> TYPE: PRT
<213> ORGANISM: Hepatitis C Virus

<400> SEQUENCE: 96

Pro Ile Pro Lys
 1

<210> SEQ ID NO 97
<211> LENGTH: 4
<212> TYPE: PRT
<213> ORGANISM: Hepatitis C Virus

<400> SEQUENCE: 97

Ile Pro Lys Ala
 1

<210> SEQ ID NO 98
<211> LENGTH: 8
<212> TYPE: PRT
<213> ORGANISM: Hepatitis C Virus

<400> SEQUENCE: 98

Gly Pro Arg Leu Gly Val Arg Ala
 1               5
```

(Gln Pro Ile Pro appears at the top, continued from previous page, numbered 1.)

What is claimed is:

1. A method for detection of hepatitis C virus core protein and antibodies to hepatitis C virus core protein in a sample comprising the steps of:
   a) contacting said sample with a first capture peptide consisting of SEQ ID NO:4, a second capture peptide consisting of SEQ ID NO:3 or SEQ ID NO:54, and a third capture peptide consisting of SEQ ID NO:5 under conditions that allow formation of capture peptide:antibody complexes between said first, second and third capture peptides and said antibodies to hepatitis C virus core protein
      wherein each of said peptides conjugated to at least one member selected from the group consisting of a functional group, a spacer group, a carrier protein and combinations thereof,
      wherein the spacer group comprises one or more 6-aminohexanoic acid spacers, 1,3-diamino propane spacer, 1,3-diamino ethane spacer, or short polyglycine sequnces of 1 to 5 amino acids, and the carrier protein comprises bovine serum albumin, casein, or thyroglobulin;
   b) contacting said sample with a first antibody under conditions that allow formation of an antibody:antigen complex between said first antibody and said hepatitis C virus core protein, wherein said first antibody specifically binds said hepatitis C virus core protein at a first epitope comprising SEQ ID NO:6;
   c) detecting any capture peptide:antibody complexes formed in step (a) as a measure of said hepatitis C virus core protein, wherein said antibodies may be detected in the seroconversion and chronic phases of infection; and
   d) detecting any antibody:antigen complexes formed in step (b) as a measure of said hepatitis C virus protein.

2. The method according to claim 1, wherein detecting any antibody:antigen complexes in step (d) comprises contacting said antibody:antigen complexes with a second monoclonal antibody capable of specifically binding hepatitis C virus core protein at a second epitope, wherein said second epitope is different from said first epitope.

3. The method according to claim 1, wherein detecting any capture peptide:antibody complexes in step (c) comprises said capture peptide:antibody complexes with three different detection peptides which bind respectively to each of said complexes.

4. The method according to claim 1, wherein said antibody is a monoclonal antibody.

5. The method according to claim 1, further comprising the step of detecting a hepatitis C virus non-core protein.

6. The method according to claim 5, wherein said hepatitis C virus noncore protein is non-structural protein NS3.

7. The method according to claim 5, wherein said step of detecting said hepatitis C virus non-core protein comprises contacting said sample with an antibody specific for said hepatitis C virus non-core protein under conditions that allow for formation of hepatitis C virus non-core protein:antibody complexes, and detecting any hepatitis C virus non-core protein:antibody complexes formed.

8. The method according to claim 5, wherein the step of detecting a hepatitis C virus non-core protein comprises contacting said sample with an antibody specific for a hepatitis C virus non-core protein under conditions that allow for formation of antibody:hepatitis C virus non-core protein complexes.

9. The method claim 1, further comprising the step of adding an additional antibody to said sample for a time and under conditions that allow formation of an antibody:antigen complex between said additional antibody and said hepatitis C virus core protein, wherein said additional antibody specifically binds said hepatitis C virus core protein at an epitope comprising SEQ ID: 98.

10. The method of claim 1, wherein the first epitope consists of SEQ ID NO:6.

11. The method of claim 9, wherein the epitope consists of SEQ ID NO:98.

* * * * *